(12) United States Patent
Mercati

(10) Patent No.: US 10,383,905 B2
(45) Date of Patent: Aug. 20, 2019

(54) **EXTRACT OF *CYNARA* SSP. AND USES THEREOF**

(71) Applicant: ABOCA S.P.A. SOCIETA' AGRICOLA, Sansepolcro (IT)

(72) Inventor: Valentino Mercati, Sansepolcro (IT)

(73) Assignee: ABOCA S.P.A. SOCIETA' AGRICOLA, Sansepolcro AR (IT)

( * ) Notice: Subject to any disclaimer, the term of this patent is extended or adjusted under 35 U.S.C. 154(b) by 0 days.

(21) Appl. No.: 14/893,063

(22) PCT Filed: May 29, 2014

(86) PCT No.: PCT/IB2014/061815
§ 371 (c)(1),
(2) Date: Nov. 22, 2015

(87) PCT Pub. No.: WO2014/191954
PCT Pub. Date: Dec. 4, 2014

(65) Prior Publication Data
US 2016/0120923 A1    May 5, 2016

(30) Foreign Application Priority Data
May 29, 2013   (IT) .............................. RM2013A0312

(51) Int. Cl.
*A61K 36/00* (2006.01)
*A61K 36/28* (2006.01)
*A61K 45/06* (2006.01)

(52) U.S. Cl.
CPC .............. *A61K 36/28* (2013.01); *A61K 45/06* (2013.01)

(58) Field of Classification Search
CPC ...................................................... A61K 36/00
USPC ........................................................ 424/725
See application file for complete search history.

(56) References Cited

U.S. PATENT DOCUMENTS 7,008,633 B2 * 3/2006 Yang .................... A61K 9/0024
424/422
2002/0012708 A1    1/2002 Ruepp

FOREIGN PATENT DOCUMENTS

WO    2007/006391    1/2007
WO    2009/040778    4/2009

OTHER PUBLICATIONS

Int'l Search Report for PCT/IB2014/061815, five pages (dated Oct. 2014).
Written Opinion for PCT/IB2014/061815, seven pages (dated Oct. 2014).
Conforti et al. "Antiproliferative activity against human tumor cell lines and toxicity test on Mediterranean dietary plants" *Food and Chemical Toxicology*, vol. 46, No. 10, pp. 3325-3332 (Oct. 2008).
Nadova et al. "Growth inhibitory effect of ethyl acetate-soluble fraction of Cynara cardunculus L. in leukemia cells involves cell cycle arrest, cytochrome c release and activation of caspases" *Phytotherapy Research*, vol. 22, No. 2, pp. 165-168 (Feb. 2008).
Okudaira et al. "Involvement of retrotransposition of long interspersed nucleotide element-1 in skin tumorigenesis induced by 7,12-dimethylbenz[a]anthracene and 12-O-tetradecanoylphorbol-13-acetate" *Cancer Science*, vol. 102, No. 11, pp. 2000-2006 (Nov. 2011).
Yasukawa et al. "Inhibitory effect of the flowers of artichoke (*Cynara cardunculus*) on TPA-induced inflammation and tumor promotion in two-stage carcinogenesis in mouse skin" *Journal of Natural Medicines*, vol. 64, No. 3, pp. 388-391 (Mar. 2010).

* cited by examiner

*Primary Examiner* — Michael V Meller
(74) *Attorney, Agent, or Firm* — Sterne, Kessler, Goldstein & Fox P.L.L.C.

(57) ABSTRACT

The present invention relates to an extract of *Cynara* spp. and also to compositions and kits that comprise said extract for the prevention and/or the treatment of a pathological condition characterized by a constitutive activation of the STAT3 transcription factor.

3 Claims, 21 Drawing Sheets

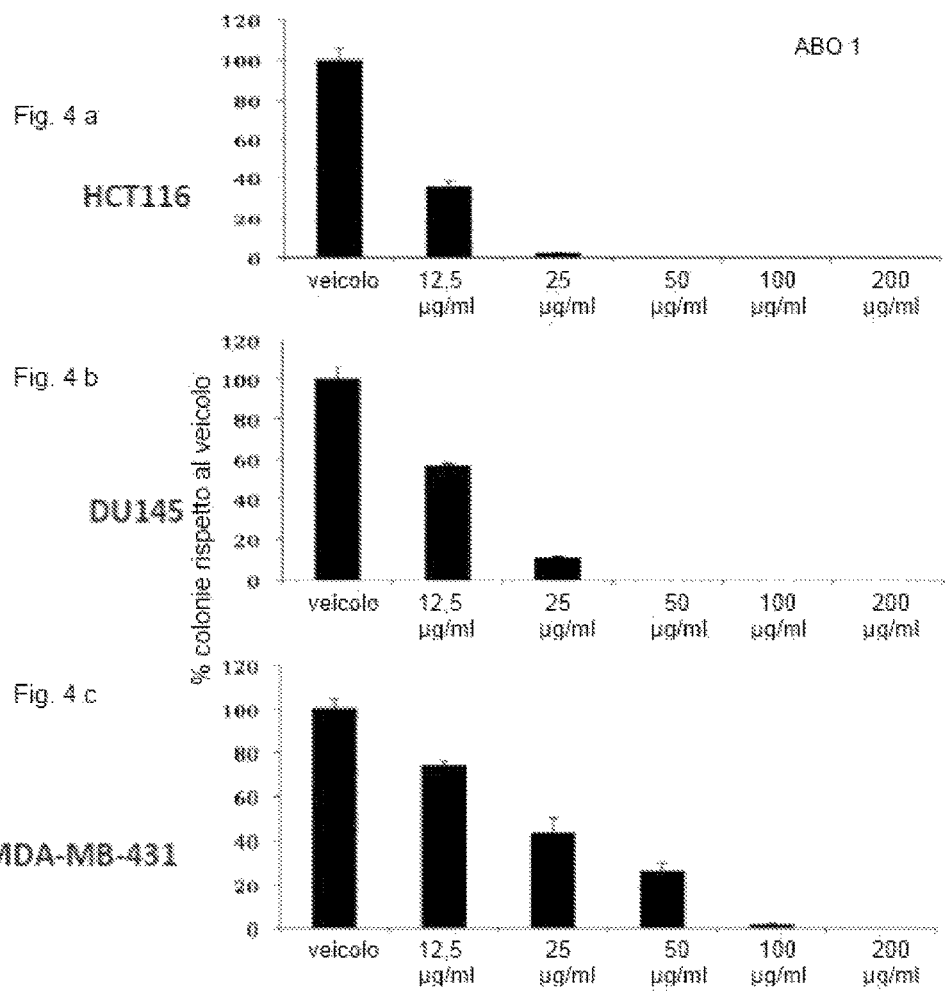
Fig. 4 a-c

EXTRACT OF *CYNARA* SSP. AND USES THEREOF

This application is the U.S. national phase of International Application No. PCT/IB2014/061815, filed 29 May 2014, which designated the U.S. and claims priority to Italian Application No. RM2013A000312, filed 29 May 2013; the entire contents of each of which are hereby incorporated by reference.

TECHNICAL FIELD OF THE INVENTION

The present invention relates to an extract of *Cynara* spp. and to compositions and kits that comprise said extract for the prevention and/or the treatment of a pathological condition characterised by a constitutive activation of the STAT3 transcription factor.

PRIOR ART

In recent decades, much evidence in literature indicates the fundamental role of transcription factors belonging to the STAT family in a wide variety of pathologies, such as in inflammatory pathologies that promote tumours, and in tumours themselves. STAT proteins are cytoplasmic transcription factors of which the phosphorylation/activation (on specific residues of serine and/or tyrosine due to the action of the families of JAK, or Janus kinase proteins) determines the dimerization of two STAT monomers, the translocation of the dimer in the nucleus, the binding to elements of the DNA of STAT-specific target genes, and the induction of gene transcription. The family of the STAT factors consists of seven members (coded by the genes STAT1, STAT2, STAT3, STAT4, STAT5A, STAT5B and STAT6) with various biological functions that include roles in differentiation, proliferation, development, apoptosis and cell inflammation. One characteristic of the proteins coded by these genes is that of having a dual role, more specifically a role of transduction of the signal in the cytoplasm and of transcription factor in the nucleus. In particular, a constitutive activation of STAT3 and to a lesser extent of STAT5 has been associated in various neoplasias with the deregulation of some intracellular pathways, including those involved in the survival of the tumour and in the proliferation of the tumour cell, but also in the process of angiogenesis and metastasis of the tumour itself.

Yu H. et al in a review published on Nature in 2009 (Nature Reviews Cancer 9, 798-809: 2009) reported that the persistent activation of STAT3 induces inflammation that promotes the cancer and regulates genes crucial for the inflammation and the tumour microenvironment. Genes activated by STAT3 are shown in Tables 1 and 2 of the above-mentioned work, and some inhibitors of the activation of STAT3 are also described among natural substances, such as curcubitacin, resveratrol, galiellalactone and indirubin, however it is stated that the mechanisms of actions by which these substances act are unknown.

In any case, the work states that the modulation of STAT3 is a new, more effective and highly advantageous approach for treating cancer, reporting that the ablation of the STAT3 gene in various tumour models led to inhibition of tumour growth.

The constitutive activation of STAT3 has been reported in a large number of tumours, including breast cancer, prostate cancer, squamous-cell carcinoma of the head and neck, multiple myeloma, lymphoma and leukaemia, brain tumours, colon cancer, Ewing's sarcoma, stomach cancer, oesophageal cancer, ovarian cancer, nasopharyngeal cancer, and pancreatic cancer (Table 1 below). For many types of cancer, high levels of activated STAT3 have been linked to a poor prognosis. The activation of STAT3 blocks apoptosis and increases cell proliferation and cell survival, promoting angiogenesis and metastasis and inhibiting the anti-tumour immune responses. Tumour cell lines in which STAT3 is constitutively activated require the continuous activation of STAT3, a phenotype that has been defined as "dependence on oncogenes" (Johnston P A and Grandis R G, MolInterv; 11 (1); 18-26:2011).

Malignant plural mesothelioma (MPM) is an aggressive tumour derived from the mesothelial cells of the chest cavities, and, although chemotherapy (often if pemetrexed is used) improves the survival time in patients with non-operable MPM, the average global survival time is just 12 months. It has been reported recently that a potential molecular therapeutic target for MPM is the interleukine-6 signalling pathway (IL-6)/JAK/STAT3 activated by the high level of IL-6 present in pleural liquid of patients with MPM. The bind of IL-6 to its receptor causes a conformational change in the receptor that initiates JAK activation, which in turn initiates the dimerization of the STAT3 transcription factor, and the STAT3 dimer translocates in the nucleus, thus determining the initiation of the transactivation of various target genes.

This pathway is key for the occurrence of haematopoiesis, of the immune response and of oncogenesis. In addition, it has also been demonstrated that the dysfunction of the JAK/STAT3 system is involved in the development of cancer.

It has been reported in the literature that the exposure to asbestos is one of the causes of mesothelioma.

It is also expected that the incidence of mesothelioma in developed countries will rise in the next 15 years, and some projections have predicted a doubling of the cases of hMPM each year between 1998 and 2018. A dramatic rise of mesothelioma in the third world is also expected, in particular in India, where the use of asbestos continues to rise exponentially without the necessary precautions being taken. Currently, the cases of mesothelioma cause approximately 3,000 deaths per year in the USA and approximately 5,000 in Europe. In spite of the programs of asbestos elimination, the frequency of mesothelioma has not changed significantly in the last 20 years and it is estimated that it will rise by 5%-10% per year in European countries in the next 25 years.

The WHO estimates that approximately 125 million people are exposed to asbestos in the workplace.

In the United States, the total predicted number of cases of mesothelioma in the male population over the course of 50 years is estimated to be equal to 71,000.

In Europe, where the commercial use of asbestos has been banned for years, a first analysis has predicted that the deaths caused by mesothelioma in the male population will continue to rise with a maximum peak around 2020, or, in accordance with more recent predictions, around 2015 (considering an average latency of 44.6 years).

The annual incidence of the disease varies according to country, however it is suspected that in the emerging markets the number of cases will rise dramatically due to the lack of regulation in asbestos mines and the proliferation of the use of asbestos at industrial and domestic level.

hMPM is typically classified into 4 sub-groups, and various prognostic factors have been identified. Current therapies include surgery, radiation, chemotherapy and multimodal therapy, but until now have brought rather disappointing results. Mesothelioma is very rarely suitable for radical surgical resection and its resistance to chemotherapy and to radiotherapy is commonly reported in the literature. Survival from the moment of diagnosis is 8-18 months.

In addition, a broad description of the role played by STAT3 in the development and in the progression of the tumour is ever present in the literature. A constitutive activation of STAT3 has been observed both in blood tumours (multiple myeloma, leukaemia, lymphoma) and in solid tumours (melanomas, carcinoma of the ovaries, of the prostate and of the renal cells, pancreatic adenocarcinoma, lung cancer and brain cancer). For greater depth, Table 3 below, taken from Turkson J and Jove R, Oncogene; 19(56); 6613-26: 2000, indicates numerous tumours directly associated with the anomalous activation of STAT3. In particular, this anomalous activation seems to be caused by the action of transforming tyrosine kinases, such as v-Src, v-Ros, v-Fps, Etk/BMX and Lck, or by an anomalous signal induced by the autocrine or paracrine release of cytokines. The constitutive activation of STAT3 leads to a greater expression of genes coding for inhibitors of apoptosis (for example Bcl-xL, Mcl-1), regulators of the cell cycle (for example cyclin D1/D2, c Myc) and inducers of angiogenesis (for example VEGF: Vascular Endothelial Growth Factor). Lastly, it has been demonstrated recently that apart from having a key role in tumourigenesis, the constitutive activation of this transcription factor confers resistance to the death induced by chemotherapeutic agents (Aggarwal B. B. et al. Ann. N.Y. Acad. Sci. 1091; 151-69: 2006).

A variety of clinical research has demonstrated that, in vivo, solid tumours grow and develop in an environment with low levels of O2 that make the tumour itself insensitive to the signals of cell death and resistant to radiotherapy and chemotherapy treatments; on the other hand, the hypoxia promotes angiogenesis, proliferation and metastatic ability. The aggressiveness of the tumour in this context seems to be associated with the activation and stabilisation of the factor of HIF-1α both by the hypoxia and by the hyperactivation of STAT3.

For this reason, an anti-cancer therapy based on the targeting of the factor STAT3 is highly desirable (Niu G. et al. Mol Cancer Res, 6 (7); 1099-105: 2008).

Table 1, shown below, is taken from the work of Aggarwal B. B. et al. 2006 and shows a list of tumours that express constitutively active STAT3, activators of STAT3, genes regulated by STAT3 and inhibitors of STAT3

TABLE 1

| Constitutive STAT3 | Activators | Genes | Kinases | Inhibitors |
|---|---|---|---|---|
| Haematopoietic tumours | EGF | Antiapoptosis | Non-receptor | Synthetic |
| Multiple myeloma | IL-6 | Bcl-$x_L$ | tyrosine kinases | AG490 |
| HTLV-1-dependent | IL-5 | Bcl-2 | JAK | Sodium salicylate |
| leukaemia | IL-9 | Mcl-1 | JAK2 | Atiprimod |
| CLL | IL-10 | cIAP-2 | JAK3 | BMS-354825 |
| CML | IL-12 | Survivin | TYK2 | Ethanol |
| AML | IL-22 | Cell cycle | Src | Nelfinavir |
| Large granular lymphocyte | TNF- | progression | Receptor tyrosine | PS-341 |
| leukaemia | MCP-1 | Cyclin D1 | kinases | R115777 |
| Erythroleukaemia | GCSF | c-Myc | EGFR | WP-1034 |
| Polycythaemia vera | GMCSF | c-Fos | ErbB-2 | Platinum compounds |
| EBV-related/Burkitt's | CSF | p21 | Gp130 | 15-Deoxy-delta |
| Mycosis fungoides | LIF | Tumour invasion and | Grb2 | 12,14-PGJ2 |
| Cutaneous T cell lymphoma | OSM | metastasis | Serine kinases | UCN-01 |
| HSV saimiri-dependent (T | IFN- | MMP-2 | JNK | Statin |
| cell) | MIP-1 | MMP-9 | P38MAPK | Peptides |
| Hodgkin's disease | RANTES | catenin | ERK | SOCS3 |
| Anaplastic lymphoma | SLF | VEGF | Tyrosine | PIAS |
| Solid tumours | UVB | hTERT | phosphatase | GRIM-19 |
| Breast cancer | Osmotic shock | IRF-1 | SHP2 | Adiponectin |
| Brain tumour | Progestin | NLK | | Duplin |
| Colon carcinoma | LPS | MyD88 | | SSI-1 |
| Ewing's sarcoma | Tobacco | RANKL | | Thrombin |
| Gastric carcinoma | HCV | TNF | | Lipoxin A4 |
| Lung cancer | | macroglobulin | | DIF-1 |
| Nasopharyngeal cancer | | SOCS | | PTP C |
| Ovarian carcinoma | | Angiotensinogen | | STAT3-DN |
| Pancreatic adenocarcinoma | | Antichymotrypsin | | Decoy peptide |
| Prostate carcinoma | | | | Naturals |
| Renal cell carcinoma | | | | Flavopiridol |
| SCCHN cancer | | | | Indirubin |
| | | | | Magnolol |
| | | | | Resveratrol |
| | | | | Piceatannol |
| | | | | Parthenolide |
| | | | | EGCG |
| | | | | Curcumin |
| | | | | Cucurbitacin |
| | | | | Others |
| | | | | Rituximab |
| | | | | GQ-ODN |
| | | | | Retinoic acid |

TABLE 1-continued

| Constitutive STAT3 | Activators | Genes | Kinases | Inhibitors |
|---|---|---|---|---|
| | | | | STA-21 |
| | | | | EKB569 |

Key:
STAT, signal-transducer-and-activator-of-transcription;
CLL, chronic lymphocytic leukaemia;
CML, chronic myeloid leukaemia;
AML, acute myelogenous leukaemia;
SCCHN, squamous cell carcinoma of the head and neck;
HTLV, human T cell lymphotropic virus;
EBV, Epstein-Barr virus;
Nelfinavir, HIV-1 protease inhibitor;
R115777, farnesyl transferase inhibitor;
AG490 and piceatannol, tyrosine kinase inhibitors;
PIAS, protein inhibitor of activated STAT3;
GQ-ODN, G-quartet oligonucleotides;
SOCS, suppressor of cytokine signalling;
GRIM, gene associated with retinoid-IFN-induced mortality;
EGCG, epigallocatechin-3-gallate;
SSI, STAT-induced STAT inhibitor;
PTP C, protein tyrosine phosphatase C;
DN, dominant negative;
EKb-569, EGF-R inhibitor;
DIF-1, differentiation-inducing factor-1;
JAB, SH2-domain-containing protein;
IL, interleukin;
TNF, tumour necrosis factor;
MDA, melanoma differentiation antigen;
MCP, monocyte chemoattractant protein;
GCSF, granulocyte colony-stimulating factor;
LIF, leukaemia inhibitory factor;
OSM, oncostatin M;
IFN, interferon;
MIP, macrophage inflammatory protein;
RANTES, regulated upon activation, normal T cell expressed and secreted;
EGF, epidermal growth factor;
LPS, lipopolysaccharide;
VEGF, vascular endothelial growth factor;
MMP, matrix metalloproteinase;
hTERT, human telomerase reverse;
SLF, steel factor;
HCV, hepatitis C virus Table 2 is taken from Johnston P A and Grandis R G 2011 and correlates STAT3 with numerous tumours, confirming the fact that STAT3 is effectively a target of interest for anti-cancer therapies.

TABLE 2

| Characterisation of tumours with increased expression of STAT3 and activity | Inauspicious prognosis correlated with high level of STAT3 | Abnormality upstream and downstream of the signal of STAT3 | Models of xenotransplantation responsive to the inhibition of STAT3 |
|---|---|---|---|
| Leukaemia | Carcinoma of the kidney cells | Elevated expression of EGFR | Squamous-cell carcinoma of the head and neck |
| Lymphoma | Colorectal cancer | Constitutively activated EGFR-RTK | Glioblastoma |
| Multiple myeloma | Ovarian carcinoma | Overexpression of SFK | Myeloproliferative neoplasms |
| Breast cancer | Gastric carcinoma | Hyperactivated JAK | Carcinoma of the renal cells |
| Prostate carcinoma | Intestinal-type gastric adenocarcinoma | Elevated levels of TNF-/IL-6 | Breast cancer |
| Lung cancer | Squamous-cell carcinoma of the cervix | | Lung adenocarcinoma |
| Lung cancer (not small cell) | Osteosarcoma | | Acute lymphoblastic leukaemia |
| Carcinoma of the renal cells | Epithelial carcinoma of the ovary | | |
| Hepatocellular carcinoma | | | |
| Cholangiocarcinoma | | | |
| Ovarian carcinoma | | | |
| Pancreatic adenocarcinoma | | | |
| Melanoma | | | |
| Squamous-cell carcinoma of the head and neck | | | |

Table 3, taken from Turkson J and Jove R 2000, indicates numerous tumours associated directly with the anomalous activation of STAT3.

TABLE 3

| Type of tumour | activated STATs | References |
|---|---|---|
| Breast tumours | | |
| Tumours | STAT 1, 3 | (Garcia et al., 2000; Watson and Miller, 1995) (J Bromberg and JE Darnell, unpublished results; P Chaturvedi and EP Reddy, unpublished results; R Garcia, C Muro-Cacho, S Minton, C Cox, N Ku, R Falcone, T Bowman and R Jove, unpublished results) |
| cells | STAT 3 | (Garcia et al., 1997; Sartor et al., 1997) |
| Neck and head tumours | | |
| Cell lines and tumours | STAT 1, 3 | (Grandis et al., 1998, 2000a) |
| Malignant melanomas | | |
| Cell lines and tumours | STAT 1, 3 | (Florenes et al., 1999; Kirkwood et al., 1999; Pansky et al., 2000) |
| Pituitary tumours | | |
| Cell lines | STAT 1 | (Ray et al., 1998) |
| Brain tumours (primary tumours | | |
| Gliomas | STAT 1, 3 | (Cattaneo et al., 1998) |
| Medulloblastomas | STAT 3 | (Cattaneo et al., 1998) |
| Brain meningiomas | STAT 1, 3, 5 | (Magrassi et al., 1999; Schrell et al., 1998) |
| Multiple myelomas | | |
| Cell lines and tumours | STAT 1, | (Catlett-Falcone et al., 1999b) |
| Lymphomas (cell lines and tumours) | | |
| Large T-cell anaplastic lymphoma | STAT 3, 5 | (Zhang et al., 1996c) |
| Sezary syndrome | STAT 3, 5 | (Zhang et al., 1996c) |
| EBV-related/Burkitt's HSV lymphoma | STAT 3 | (Weber-Nordt et al., 1996) |
| Saimiri-dependent HSV (T-cell) | STAT 3 | (Lund et al., 1997b, 1999) |
| T-cell cutaneous lymphoma | STAT 3 | (Sun et al., 1998) |
| LSTRA T-cell lymphoma (mouse) | STAT 5 | (Yu et al., 1997) |
| Mycosis fungoides | STAT 3 | (Nielsen et al., 1997) |
| Leukaemias (tumours and cell lines) | | |
| HTLV-I dependents | STAT 3, 5 | (Migone et al., 1995; Takemoto et al., 1997) |
| Chromic lymphocytic leukaemia (CLL) | STAT 1, 3 | (Frank et al., 1997) |
| Acute myeloid leukaemia (AML) | STAT 1, 3, 5 | (Chai et al., 1997; Gouilleux-Gruart et al., 1996; Weber-Nordt et al., 1996) |
| Megakaryocytic leukaemia | STAT 1, 3, 5 | (Liu et al., 1999) |
| Large granular lymphocytic leukaemia (LGL) | STAT 3 | (Epling-Burnette et al., 2000) |
| OTHER TUMOURS (tumours and cell lines) | | |
| Prostate | STAT 3 | L Mora, R Garcia, J Seigne, T Bowman, M Huang, G Niu, J Pow-Sang, J Diaz, C Muro-Cacho, D Coppola, T Yeatman, J Cheng, S Nicosia, S Shivers, T Landowski, D Reintgen, W Dalton, H Yu and R Jove, unpublished results |
| Renal cell carcinoma | STAT 3 | |
| Ovarian carcinoma | STAT 3 | |
| Melanoma | STAT 3 | |

In particular, in relation to STAT3, the following has been demonstrated in numerous publications:

1) STAT3 is often constitutively active (phosphorylated) in many human cancer cells, such as multiple myeloma, lymphoma, leukaemia, lung cancer, prostate cancer, squamous-cell carcinoma cells of the head and neck, and other tumour types.

2) STAT3 is activated by growth factors (for example EGF, TGF-, IL-6, IL-10, IL-23, IL-21, IL-11, HGF), kinase oncogenics (for example Src). 3) STAT3 mediates the expression of proliferation genes (for example c-myc, cyclin D1), of apoptosis suppressor genes (for example Bcl-XL and survivin), of cytokine coding genes, and of genes that promote angiogenesis (for example VEGF), increasing, when activated, cell proliferation and angiogenesis and inhibiting apoptosis.

4) The activation of STAT3 also correlates with phenomena of chemoresistance and radioresistance.

5) The persistent activation of STAT3 increases, in various human cancers, proliferation, survival, angiogenesis and metastasis and inhibits anti-tumour immunity.

It is also known that chronic inflammation in certain organs or at certain sites promotes malignant transformation, and that STAT3 is crucial for the extrinsic and intrinsic pathways of inflammations that lead to cancer, STAT3 being known in fact to guide the malignant characteristics associated with chronic inflammation.

Due to the crucial role of STAT3 in tumourigenesis, the inhibitors of STAT3 have enormous potential in the prevention and in the treatment of cancer. Perhaps one of the best-known inhibitors of the activation of STAT3 is AG490, which inhibits the activation of JAK2. Other inhibitors of STAT3 include small peptides, oligonucleotides, and small molecules. Some authors have identified peptides that block the phosphorylation/activation of STAT3, this being a mechanism that mediates the binding to the DNA and the activity of gene regulation, and cell transformation. Various small molecules that block STAT3 include PGJ2, complexes of platinum, ethanol, sodium salicylate, retinoic acid, atiprimod, PS-341 and statins. Many polyphenol plants have been identified for their ability to suppress the activation of STAT3. These include curcumin, resveratrol, cucurbitacin, piceatannol, parthenolide, flazopiridol, magnolol, and epigallocatechin-3-gallate. The way in which these molecules succeed in suppressing the activation of STAT3 is not entirely clear. For example, curcumin has demonstrated the effect of inhibition of JAK2, Src, Erb2 and EGFR, which are all involved in the activation of STAT3, also downregulating the expression of Bcl-xL, cyclin D1, VEGF, and TNF, of which the expression is regulated by STAT3 (Aggarwal B. B. et al. Ann. N.Y. Acad. Sci. 1091; 151-69: 2006).

There are thus various strategies and various mechanisms that make it possible to intervene in the cascade of signalling of STAT3: inhibiting the phosphorylation/activation of STAT3, inhibiting the intermolecular interactions that involve STAT3, inhibiting the nuclear import/export of STAT3, inhibiting the transcription mediated by STAT3. Apart from the chemotherapeutic agents already mentioned that inhibit STAT3, there are also others (cetuximab, gefitinib, erlotinib, etc.), for which different effects have been reported: a modest efficacy, the development of resistances, myelosuppression, toxicity at gastro-intestinal level, and various adverse events including cardiovascular toxicity (see Table 4).

Table 4, below, taken from Johnston P A and Grandis R G 2011, reports strategies and results for the therapeutic intervention of the signal of STAT3.

TABLE 4

| Strategy | Target | Examples | Results |
| --- | --- | --- | --- |
| Inhibition of the phosphorylation/activation of STAT3 | EGFR competitiveness Activity TKR Activity JAK Activity SFK | Cetuximab, panitumumab, Gefitinib, erlotinib, lapatinib, AG490, LS-104, ICNB1824, CEP-701, Dasatinib, AZD0530, basutinib | Modest efficacy; development of resistances; myelosuppression; gastro-intestinal (GI) toxicity and adverse effects; kinase selectivity and cardiovascular toxicity |
| Inhibit the intermolecular interactions that involve STAT3 | SH-2 domains of STAT3 | Designated oligopeptides from EGFR, gp130, and other receptors or peptides containing pY; octamer peptides, quartet of G oligonucleotides; small peptidomimetic molecules | Scarce cell permeability and efficacy; scarce metabolic stability; scarce selectivity for specific SH2 domains; potential adverse events |
| Inhibit the nuclear import/export of STAT3 | Imports 3, 5, 7 Import Export 1 | Karyostatin 1A (non-determined effects on STAT3), Leptomycin B and Ratjadone A | Multi-component nature of the nuclear pore and incompletely determined translocation; problematic specificity for the translocation of the proteins |
| Inhibition of STAT3 mediated transcription | Not specified | dsODNdecoy; octamer peptides | Scarce cell permeability without effective and specific distribution systems; scarce metabolic stability |
| Natural products | Not specified | Guggulsterone, honokiol, curcumin, resveratrol, flavopiridol, cucurbitacin | Unknown specificity, power, efficacy and mechanism of action |

Therapies that are targeted therapies by means of compounds that inhibit a specific target molecule in a more specific manner, in sub-populations of cells directly involved in tumour progression, represent a new perspective in the treatment of cancer. The molecules that control cell proliferation and death, such as receptor tyrosine kinases (RTKs) for growth factor are among the best objectives of this type of therapeutic approach. The era of targeted therapy started with the approval of trastuzumab, a monoclonal antibody against HER2, for the treatment of metastatic mammary carcinoma and imatibin, an inhibitor of BCR-ABL, in chronic myeloid leukaemia. In spite of the initial enthusiasm for the efficacy of these treatments, the doctors had to immediately confront the problem of relapse, since those suffering from cancer almost always developed a resistance to the drugs, often due to the activation of alternative pathways. Since the tumour is characterised by more mechanisms and more gene targets, which are frequently deregulated, it would be advantageous to adopt a combination therapy, as is standard in the treatment of cancer, since this results in a rational strategy for increasing the response and the tolerability and for decreasing resistance. There is currently a rise in interest for the combination of anti-tumour drugs that aim to maximise efficacy, minimising the systemic toxicity by means of the use of lower drug doses.

Thus, pharmacologically safe and effective therapeutic agents, such as molecules of natural origin, which can block constitutive or inducible activation of STAT3, have a potential efficacy in the treatment of cancer, given that more and more tests are concluding that the inhibition of the phosphorylation of STAT3 by means of a pharmacological blocking of the molecules upstream, including Src and JAK, can reduce the formation of tumours, also leading to the possibility of reduction of the necessary dosage of chemotherapeutic drug.

In addition, since the activation of STAT3 also correlates with the resistance to chemotherapy and radiotherapy, inhibitors of such activation are also of great interest for limiting such resistance and optimising the effect of chemotherapy and of radiotherapy.

SUMMARY OF THE INVENTION

The authors of the present invention have demonstrated that extracts of artichoke (*Cynara* spp.) are able to selectively modulate, essentially inhibit, the phosphorylation of the protein STAT3, consequently preventing the subsequent action within the cell as transcription factor. As will be seen in the experimental part of the application, the authors of the invention have demonstrated, in numerous experiments and on various cell lines of malignant pleural mesothelioma, that the extracts described here are effective inhibitors of the activation (phosphorylation) of STAT3 and consequently

- demonstrate effective cytotoxic action on tumour cell lines,
- are able to inhibit the regeneration of tumour cells, thus acting as cytostatics,
- induce apoptosis in tumour cells
- have additive and also synergistic effects with numerous chemotherapeutic agents, thus resulting in a reduction of the vitality of the tumour cells compared with those treated with the chemotherapeutic agent alone or with the extract alone
- act in a differential manner on malignant pleural mesothelioma cells and on untransformed mesothelial cells.

From the viewpoint of the effect of such extracts on the STAT3 factor, the authors of the present invention have also demonstrated by way of experiment that the extracts of *Cynara* spp. described here are able to prevent the binding of STAT3 to the DNA and thus to prevent the alteration of the expression of the genes normally activated by phosphorylated STAT3.

In other words, said extract has proven to be capable of modulating, essentially inhibiting, the protein STAT3 in its phosphorylated form, preventing the successive action of said protein within the cell as transcription factor. In particular, the inventors of the present disclosure have demonstrated that an extract of *Cynara* spp. is able to inhibit the constitutive or anomalous activation of STAT3 and to induce the reactivation of apoptosis in cultures of MPM tumour cells. In addition, the authors of the present invention have also demonstrated that, in experiments on cultures of MPM tumour cells, the extract of *Cynara* spp. inhibits wound healing, in fact preventing the invasivity of the tumour cells. In addition, the authors of the present invention have also demonstrated with experiments of engraftment of tumour cells in mice that the extract of the present invention exerts in vivo an anti-tumour effect with respect to MPM cells.

In all embodiments of the present invention, MPM can be substituted with the term hMPM A first subject of the present invention is therefore an extract of *Cynara* spp. for use in the prevention and/or in the treatment of an inflammatory and/or pre-tumour and/or tumour pathological condition characterised by a constitutive or anomalous activation of the STAT3 transcription factor.

A second subject of the present invention is an extract of *Cynara* spp. for use in the prevention and/or in the treatment of an inflammatory and/or pre-tumour and/or tumour pathological condition characterised by a constitutive or anomalous activation of the STAT3 transcription factor in association with one or more chemotherapeutic agents. A third subject of the present disclosure is a composition comprising an extract of *Cynara* spp. and a carrier and/or diluent and/or excipient for use in the prevention and/or in the treatment of an inflammatory and/or pre-tumour and/or tumour pathological condition characterised by a constitutive or anomalous activation of the STAT3 transcription factor.

In one embodiment, the composition also comprises one or more components with anti-apoptotic components.

A fourth subject of the present invention is a composition comprising an extract of *Cynara* spp. in association with one or more components with anti-tumour and/or anti-inflammatory components and a carrier and/or diluent and/or excipients for use in the prevention and/or in the treatment of an inflammatory and/or pre-tumour and/or tumour pathological condition characterised by a constitutive or anomalous activation of STAT3 transcription factor.

A fifth object of the present invention is a kit for concomitant or sequential administration of an extract of *Cynara* spp. and one or more chemotherapeutic agents comprising one or more aliquots of an extract of *Cynara* spp. or of a composition comprising an extract of *Cynara* spp. and one or more separate aliquots of one or more compositions comprising a chemotherapeutic agent for use in the prevention and/or in the treatment of an inflammatory and/or pre-tumour and/or tumour pathological condition characterised by a constitutive or anomalous activation of STAT3 transcription factor in association with a chemotherapeutic agent.

A sixth subject of the invention is a therapeutic method for the prevention and/or in the treatment of an inflammatory and/or pre-tumour and/or tumour pathological condition characterised by a constitutive or anomalous activation of the STAT3 transcription factor comprising the step of administering to an individual who needs it a therapeutically active quantity of extract of *Cynara* spp., optionally in association with one or more components having anti-tumour and/or anti-tumour activity.

All the subjects described may concern in particular the case in which said pathological condition is associated with the formation of malignant pleural mesothelioma or is malignant pleural mesothelioma.

DETAILED DESCRIPTION OF THE FIGURES

Note: In the present figures, the extract of *Cynara* spp. used is often indicated by the abbreviation ABO-1.

FIG. 1: Inhibition of the phosphorylation of STAT3, p-STAT3 (Y705)

FIG. 1A Western Blot analyses of cell lysates obtained from MSTO211H treated with 100 µg/ml of *Cynara scolymus* extract for 24 hours. Quantification was performed compared with a control of Actina.

FIG. 1B Bar chart of the data obtained with Western Blot on MSTO211H cells. p-STAT3 (phosphorylated STAT3) is shown in black, STAT3 is shown in grey.

The figure shows that the extract inhibits the formation of p-STAT3 compared with the control.

FIG. 2: Western Blot analyses of cell lysates of MSTO211H cells treated with 25-50-75 µg/ml of *Cynara scolymus* extract in the p-STAT3 row, with the Actina control below. The figure shows that the extract inhibits STAT3 phosphorylation and that this inhibition is dose-dependent.

FIG. 3: Clonogenic assay (see the experimental section for the conditions) on cell lines of human malignant pleural mesothelioma with various doses of extract of *Cynara scolymus* graph 3a. assay performed on human mesothelioma cell line MSTO211H graph 3b. assay performed on human mesothelioma cell line NCI-H28 graph 3 c. assay performed on human mesothelioma cell line MPP-89 graph 3d. assay performed on human mesothelioma cell line NCI-H2052

FIG. 4: The extract of the invention influences the ability of 3 different inflammatory tumour lines (HCT116, MDA-MB-231 E DU145) to form colonies, in a dose-dependent manner, independently of the isotypes thereof.

graph 4a. assay performed on colon tumour cell line HCT116 graph 4b. assay performed on prostate tumour cell line DU145 graph 4c. assay performed on breast tumour cell line MDA-MB-231

FIG. 5: Assay of cell vitality using ATPlite test (see the experimental section for the conditions) on malignant pleural mesothelioma cell lines (MSTO211H, MPP-89, NCI-H28). The assay shows that cell vitality is inhibited by the extract of *Cynara scolymus* of the invention in a dose-dependent manner in various mesothelioma cell lines.

FIG. 6: comparison of the three vitality curves of FIG. 5 compared with (FIG. 6a MSTO211H, FIG. 6b MMP-89, FIG. 6c NCI-H28) the proliferation curve obtained treating normal mesothelioma cells (HMC) with extract of *Cynara scolymus*. The malignant mesothelioma cell lines (MPMs) clearly show the anti-proliferative effect of the extract of *Cynara scolymus* compared with the HMCs.

FIG. 7 Assay of cell vitality in the confluent prostatic adenocarcinoma cell line DU-145, treated with various concentrations of artichoke extract (50-600 µg/ml) for various treatment times (24 and 48 hours) with indications of the content in cynaropicrin of the extract. The confluency of the cells increases the levels of constitutively activated STAT3, making the cells themselves largely resistant to death. The vitality was analysed using the WST-1 assay (test WST-1, see the experimental section for the conditions). The figure shows that the extract inhibits vitality in a time-dependent and dose-dependent manner. The squares show the trend over 24 hours and the circles show the trend at 48 hours with extract doses from 0 to 600 µg/ml and the respective content in cynaropicrin, expressed both in µg/ml and in µM, of the extract at the various concentrations (100, 200, 300, 400, 500, 600 µg/ml).

Cells with high levels of activation of STAT3: the results obtained show that the extract inhibits cell vitality with $EC_{50}=380$ microg/ml at 24 hours and $EC_{50}=100$ µg/ml at 48 hours.

FIG. 8. Assay of cell vitality in the confluent prostatic adenocarcinoma cell line DU-145, treated with various concentrations of cynaropicrin (0-70 µm) for various treatment times (24 or 48 hours). The confluency increases the levels of constitutively activated STAT3, making the cells largely resistant to death. The vitality was analysed using the WST-1 assay (test WST-1, see the experimental section for the conditions). The figure shows that cynaropicrin inhibits cell vitality in a time-dependent and dose-dependent manner. The squares show the trend at 24 hours and the triangles show the trend at 48 hours with different concentrations: 10, 20, 30, 40, 50, 60 µM of cynaropicrin.

The data presented show that cynaropicrin is less effective than the artichoke extract. The figure shows that cynaropicrin inhibits cell vitality and proliferation in a time-dependent and dose-dependent manner much less effectively compared with the artichoke extract (see FIG. 8 as a comparison). For example: to have an effect of reduction of vitality equal to approximately 90%, treatments with 50 µM for 48 hours, compared with 0.94-2.82 µM, are necessary when cynaropicrin is contained within the lyophilised extract.

FIG. 9. Assay of cell vitality in the non-confluent cell line DU-145, thus with low levels of constitutively activated STAT3, treated with various concentrations of artichoke extract and for various treatment times (24-48-72 hours). The vitality was analysed using the WST-1 assay (test WST-1, see the experimental section for the conditions). The circles denote a treatment with 50 µg/ml of *Cynara scolymus*, the squares a treatment with 100 µg/ml, and the triangles a treatment with 200 µg/ml. The figure shows how the cell vitality of the cell line DU145 is highly compromised by *Cynara scolymus* 200 µg/ml. The results obtained show that 200 µ/ml of extract inhibit cell vitality by 60% at 24 hours. As can be seen, compared with FIG. 8, with respect to experiments on cells with high levels of activation of STAT3, the $EC_{50}$ of this experiment are considerably lower (approximately 200 vs 380 µg/ml at 24 hours), thus demonstrating a greater power of the extract of the invention in cells with low level of activation of STAT3 (non-confluent). Such experiments thus confirm that the cells in which STAT3 is active have a greater degree of malignancy. The inhibition of the phosphorylation of STAT3 is the primary mechanism of reduction of cell vitality.

FIG. 10: Assay of cell vitality (ATPlite assay) following treatment with artichoke extract in association with pemetrexed (PMTX) on mesothelioma cell lines MPM (FIG. 10a MSTO211H and FIG. 10b NCI-H2052) and transformed on mesothelioma cells (FIG. 11c HMC). The treatment with PMTX is cytotoxic for the MPM cells and highly toxic for the non-tumour cells. The co-treatment of the cells with the extract of the invention+PMTX had a significant effect on cell vitality in MPM cell lines, whilst reducing the mortality caused by pemetrexed in the untransformed cells (HCM). Consequently, it is clear that the extract of artichoke of the invention makes only the tumour cells sensitive to pemetrexed.

FIG. 11 Cell vitality assay WST-1 following treatment with extract of artichoke in association with various chemotherapeutic agents: doxorubicin, taxol, cisplatinum (see experimental section for the conditions) on a human prostate tumour cell line DU145. The vitality was analysed using the WST-1 assay (test WST-1, see the experimental section for the conditions). FIG. 11a shows the cell vitality following treatment for 24 hours, with two different doses of artichoke extract (100 and 200 μg/ml), with just cisplatinum at 10 μg/ml and with artichoke extract (100 and 200 μg/ml) in association with cisplatinum at 10 μg/ml.

FIG. 11b shows cell vitality following treatment for 24 hours, with two different doses of artichoke extract (100 and 200 μg/ml), with doxorubicin at 1 μg/ml and of artichoke extract (100 and 200 μg/ml) in association with doxorubicin at 1 μg/ml on human carcinoma cells DU145.

FIG. 11c shows the cell vitality following treatment for 24 hours, with two different artichoke extracts (100 and 200 μg/ml), with taxol 300 nM, and artichoke extract (100 and 200 μg/ml) in association with taxol 300 nM on human carcinoma cells DU145.

In all the experiments the extract forming the basis of the invention enhances the cytotoxicity of the three chemotherapeutic agents with a greater efficacy in the case of cisplatinum.

FIG. 12. Assay of cell vitality after treatment with associations of artichoke extract and cisplatinum on human carcinoma cells DU145 (see experimental section for the conditions). The figure shows the comparison between treatments with artichoke extract (black), cisplatinum (light grey) and artichoke+cisplatinum (white) at various concentrations of artichoke extract and at fixed concentration of 15 μg/ml of cisplatinum.

The relative concentrations of cynaropicrin are shown in the figure.

The extract forming the basis of the invention enhances the cytotoxicity of cisplatinum with a greater effect at the dose of 200 μg/ml.

FIG. 13. Vitality assay after treatment with association of artichoke extract and doxorubicin on human carcinoma cells DU145 (see experimental section for the conditions). The figure shows the comparison between treatments with artichoke extract (black), doxorubicin (light grey), and artichoke+doxorubicin (white) at various concentrations of artichoke extract and at fixed concentration of 2 μg/ml of doxorubicin.

The relative concentrations of cynaropicrin are the same as reported in FIG. 13.

The extract forming the basis of the invention enhances the cytotoxicity of doxorubicin with a greater effect at the dose of 200 μg/ml.

FIG. 14. Vitality assay after treatment with association of cynaropicrin and cisplatinum on human carcinoma cells DU145 (see experimental section for the conditions). The figure shows the comparison between treatments with cynaropicrin (black), cisplatinum (light grey), and cynaropicrin+cisplatinum (white) at various concentrations of cynaropicrin and at fixed concentration of 15 μg/ml of cisplatinum.

It would appear that, to obtain an effect that reduces cell vitality below 20%, a molarity of cynaropicrin forty times greater than that present in the artichoke extract is necessary (see FIG. 12).

FIG. 15 Vitality assay after treatment with association of cynaropicrin and doxorubicin on human carcinoma cells DU145 (see experimental section for the conditions). The figure shows the comparison between treatments with cynaropicrin (black), doxorubicin (light grey), and cynaropicrin+doxorubicin (white) at various concentrations of cynaropicrin and at fixed concentration of 2 μg/ml of doxorubicin.

It would appear that, to obtain an effect that reduces the cell vitality below 20%, a molarity of cynaropicrin approximately twenty-five times greater than that present in the artichoke extract is necessary (see FIG. 13).

FIG. 16: Assays of wound healing on human mesothelioma cell line MSTO221H (see experimental section for the conditions).

Graph 16a shows the wound healing at 36 h in control plates with just the carrier and with product at a concentration of 6 μg/ml, whereas image 16b shows bar charts concerning the efficacy in closing the wound (quantification of the number of cells in %) treated with the extract of the invention and with carrier at the times indicated.

FIG. 17: The extract of *Cynara Scolymus* modulates the pathway of STAT3 in DU145 cells: in particular, the figure shows that the extract inhibits the constitutive activation of STAT3 in DU-145 cells and also inhibits the binding of STAT3 to DNA.

17a) Western Blot: the extract of *Cynara scolymus* (200 μg/ml) inhibits the phosphorylation of STAT3 after 2-4 hours of treatment without modifying the expression of the protein.

17b) EMSA,

EMSA: the extract of *Cynara scolymus* (200 μg/ml) inhibits the binding of STAT3 to DNA after 2-4 hours of treatment in the DU-145 cell line (FIG. 17b).

FIG. 18: The extract of *Cynara Scolymus* modulates the pathway of STAT3 in KARPAS cells: in particular, the figure shows that the extract inhibits the constitutive activation of STAT3 in KARPAS cells and also inhibits the binding of STAT3 to DNA.

18a) Western Blot: the extract of *Cynara scolymus* (200 μg/ml) inhibits the phosphorylation of STAT3 after 2-4 hours of treatment without modifying the expression of the protein in the KARPAS cell line.

18b) EMSA: the extract of *Cynara scolymus* (200 μg/ml) inhibits the binding of STAT3 to DNA after 2-4 hours of treatment in the cell line KARPAS.

The extract of *Cynara scolymus* used contains 0.181% of cynaropicrin, thus 200 μg/ml of extract contain 1.2 μM of cynaropicrin.

FIG. 19: cynaropicrin modulates the pathway of STAT3 in DU-145 cells.

Cynaropicrin inhibits in DU-145 cells both the phosphorylation of STAT3 and the ability thereof to bind to DNA with $EC_{50}=25$ μM (25 μM cynaropicrin=approximately 0.74 μg/ml)

Western Blot: 25 μM of cynaropicrin inhibit the phosphorylation of STAT3 in DU-145 cells (FIG. 19a)

EMSA: 25 microM of cynaropicrin inhibit the binding of STAT3 to DNA in DU-145 cells (FIG. 19b)

FIG. 20: cynaropicrin modulates the pathway of STAT3 in KARPAS cells.

Cynaropicrin inhibits in KARPAS cells both the phosphorylation of STAT3 and the ability thereof to bind to DNA with $EC_{50}=25$ μM (25 μM cynaropicrin=approximately 0.74 μg/ml)

Western Blot: cynaropicrin (25 μM) inhibits the phosphorylation of STAT3 in DU-145 cells (FIG. 20a)

EMSA: cynaropicrin (25 μM) inhibits the binding of STAT3 to DNA in DU-145 cells (FIG. 20b).

FIG. 21: assessment of the impact of the extract of *Cynara scolymus* on the cell cycle (FACS method). The extract induces the death of the MPM cells (MSTO211H) by means of an increase in the % of cells in sub G1 phase, both after treatment for 48 hours (FIG. 21a) and after treatment for 72 hours (FIG. 21b)

FIG. 22 Assay to assess the induction of apoptosis (Western method). The extract of the invention at the dose of 100 µg/ml induces apoptosis as demonstrated by the rise in the levels of some apoptotic markers as the cleaved form of PARP and of caspases 3 and 7 in the cell line MSTO211H.

FIG. 23 assay to assess the induction of apoptosis by means of measurement of the level of annexin V. The extract of the invention induces apoptosis in the cell line MSTO211H, as determined by the coloration of annexin V, in a time-dependent and dose-dependent manner.

FIG. 24 Analyses of the intracellular concentration of GSH (see experimental section for the conditions) following treatment with various concentrations of cynaropicrin: triangles 12.5 µM, squares 25 µM, diamonds 50 µM.

Cynaropicrin determines a time-dependent and dose-dependent reduction of the intracellular concentration of GSH.

FIG. 25 Assay of glutathionylation of STAT3 (see experimental section for the conditions). Cynaropicrin determines the glutathionylation of STAT3. Lane 1. Control, Lane 2 GSH 1 mM, Lane 3 diamide 0.5 mM, Lane 4 GSSG, Lane 5 cynaropicrin 12 microM, Lane 6 cynaropicrin 25 µM.

The data obtained in this experiment demonstrate that cynaropicrin lowers the intracellular concentration of GSH (FIG. 26) and that the variation of the redox state induces glutathionylation of STAT3, preventing the phosphorylation thereof (FIG. 27). The restoration of the physiological values of GSH, by means of pre-treatment with glutathione ethylene ester, reverses the ability of cynaropicrin to inhibit the phosphorylation of STAT3.

FIGS. 26 and 27 concern the assessment of the anti-tumour activity of the artichoke extract in the cell line MSTO211H, performed in nude female CD1 mice 6-7 weeks old (MPM tumour engraftment)

FIG. 26: Effect of artichoke on the engraftment of MPM cell lines

The MSTO211H were pre-treated with artichoke for 24 hours. Then, they were inoculated in nude CD1 mice. The pre-treatment with the artichoke extract influenced the engraftment of the tumour and induced a significant statistical difference (p=0.01) in the volume of the tumour.

FIG. 27: Effect of the artichoke extract on the transplantation of MPM cells. CD1 mice with xenograft of MSTO treated with growing quantities of artichoke extract for 3 weeks. A therapeutic dose-dependent effect was observed for the artichoke extract. Pemetrexed (PMTX) was used as positive control at a known therapeutic concentration. The figure shows the efficacy of the extract of the invention compared with the known therapeutic concentration of pemetrexed *p<0,0

DETAILED DESCRIPTION OF THE INVENTION

The present application thus relates to a use of the extract of *Cynara* spp. in the prevention and/or in the treatment of pathologies in which a constitutive or anomalous activation of the STAT3 factor is present. As indicated before, the anomalous or constitutive activation would appear to consist in an anomalous or constitutive phosphorylation of this factor with resultant inflammatory and/or tumourigenic effects both in the blood and in tissues.

In the following description, in the claims and in the drawings, the term "STAT3" denotes the transduction factor of the signal and activation of STAT3 transcription (Signal Transducer and Activator of Transcription 3). Conventionally, where reference is made to the gene, uppercase italicised letters are used, whereas the protein is indicated by non-italicised uppercase letters.

It is already known in the literature that inflammation and tumours are closely linked by oncogenic and environmental pathways, and the phosphorylation of the STAT3 factor (Signal Transducer and Activator of Transcription 3) causes activation thereof and the displacement of the nucleus where it acts as an activator of the transcription of numerous cytokines, chemokines, and other mediators associated with inflammation, thus promoting cancer.

Inhibitors of the activation of STAT3 are therefore factors that have a preventative and/or curative effect towards all those pathologies in which constitutive activation of the STAT3 factor is present. The present invention discloses for the first time the inhibitory action specific for STAT3 of extracts of *Cynara* spp.

Artichoke or *Cynara* spp. for the purposes of the present invention mean plants belonging to the *Cynara* (*Cynara* spp.) genus, in particular *Cynara cardunculus* subsp. *scolymus*.

For the purposes of the implementation of the present invention, the extract may be an extract of leaves and/or flower-heads or mixtures thereof, either fresh of dried.

The term "flower-heads" denotes the head of the flowers produced by the plant, for example the artichoke itself (part commonly used as food). The extract could be a fluid extract, or an extract lyophilised or dried by means of known drying techniques. The extract can be obtained by means of extraction with the following solvents: water, ethanol, methanol, acetone or isopropanol, in each case in pure form or in a mixture with one another. The alcohol could be methanol, ethanol, isopropanol and is preferably ethanol. The ethanol can be used in pure form or in mixture with water at the following percentages: 96%, 90%, 85%, 80%, 75%, 70%, 65%, 60%, 55%, 50%, 45%, 40%, 35%, 30%, 25%, 20%, 15%, 10%, 5%, 1%. In a non-limiting embodiment of the invention, the solvent used for the extraction could be a mixture formed by ethyl alcohol and water in a proportion of 50:50. The fluid extract could be prepared by means of hydroalcoholic extraction by percolation/digestion of the artichoke leaves in relation to drug/solvent from 1:2 to 1:100 and preferably in a ratio of 1:10. The duration of the extraction is a duration commonly used by a person skilled in the art and could be, for example, from a minimum of 4 hours to approximately 8 hours. The temperature of extraction is normally controlled and could preferably be, for example, a temperature of approximately 50° C. The evaporation of the alcohol from the hydroalcoholic extract and the subsequent drying of the aqueous concentrate could be performed by means of lyophilisation or desiccation to provide the lyophilised extract or dry extract.

The preparation of such extracts is commonly known to a person skilled in the art and does not need to be described in particular detail in the present disclosure. For the purposes of implementing the present invention, it is possible to use any extract among those indicated above, prepared in accordance with conventional techniques.

In particular, for the purposes of the present invention, the extract could also be a fraction of the extracts as described here.

In this case, a standard procedure comprises the evaporation of the alcohol present in the alcoholic extract at 50 alcoholic degrees, the removal of the substances insoluble in alcohol by means of centrifugation at 4000 rpm for 1-5 minutes, the introduction of the aqueous solution (aqueous concentrate), resulting in a chromatographic column containing the adsorption resin.

The aforementioned aqueous concentrate can in turn be obtained by suspending the dried or lyophilised artichoke extract in water at a ratio of 1:10 p/p.

The feed fluid of the resin must have suspended solids indicatively comprised between 0.2 at 1° Bix, the feed range is between 1 and 4 BV/hour and preferably 2 BV/hour. The corresponding aqueous eluate is collected and subjected to drying by means of lyophilisation or desiccation, the substances adsorbed into the resin being eluated using 96% ethyl alcohol or methanol or acetone, preferably 96% ethyl alcohol. In this last case, the alcohol eluate is subjected to desiccation or to lyophilisation after having added in this last case water at a ratio of 1:1 v/v with alcohol eluate and ethyl alcohol evaporate.

In accordance with the present invention, the extract of Cynara spp. as defined above could be used for the prevention and/or the treatment of pathologies characterised by a constitutive or anomalous activation of the STAT3 transcription factor.

Such diseases can be, for example and as noted in the literature, diseases of the inflammatory and/or pre-tumour and/or tumour type.

For the purposes of the present invention, the pathological states characterised by a constitutive or anomalous activation of the STAT3 transcription factor can be caused by viral infections (as noted in the literature), including infections by H. pylori, infections by the Hepatitis B virus, infections by HPV (human papilloma virus), infections by the Epstein-Barr virus (as reported in Yu et al 2009).

As already mentioned, the term "STAT3" thus denotes the human transcription factor "Signal transducer and activator of transcription 3", coded in humans by the STAT3 gene.

The invention concerns pathological states in humans defined in detail in the present description (for example below) in which this gene is activated constitutively or anomalously in any case.

The pre-tumour pathological states in which a constitutive or anomalous activation of STAT3 is present can be either pathological states following the ablation of a tumour, and thus pre-tumour in the sense that the tumour could reform, or pathological states in which there is a transfer from inflammation to the acquisition of malignant characteristics on the part of the cell, as reported in the literature.

In accordance with the present invention, the tumour pathological states can be any tumours characterised by a constitutive or anomalous activation of STAT3 reported in the prior art, such as: prostate cancer, multiple myeloma, lymphoma, melanoma, carcinoma of the ovaries, carcinoma of the renal cells, pancreatic adenocarcinoma, lung cancer, brain tumour, erythroleukaemia, squamous-cell carcinoma of the head and neck, colon cancer, mesothelioma (which is intended to mean malignant pleural mesothelioma or MPM).

In particular, the present invention could be suitable for the treatment of populations exposed to asbestos and therefore at risk of malignant pleural mesothelioma and for the reduction of the production of mesothelioma in such populations of patients.

More specifically, said brain tumour could be, for example, a glioma, a brain meningioma, a medulloblastoma, said lymphoma could be Sezary syndrome, EBV-associated Burkitt lymphoma, Samiri HSV-dependent lymphoma, cutaneous T-cell related lymphoma; said leukaemias may be HTLV-I-dependent leukaemia, chronic lymphocytic leukaemia (CLL), acute myelogenous leukaemia (AML), megakaryocytic leukaemia, large granular lymphocytic leukaemia (LGL).

In accordance with a non-limiting example of the present invention, the extract of Cynara spp. as defined above can be used for the prevention and/or the treatment of any one of the pathological states characterised by a constitutive or anomalous activation of STAT3 listed in Table 1 above.

The terms "constitutive activation" or "anomalous activation" according to the present invention are to be understood within the sense of the meaning attributed to such terms in the literature relating to STAT3 (for example as listed in the bibliography), or a persistent activation of this factor, usually absent in healthy cells.

Given the specificity in the inhibition of the activation and of the activity of STAT3 shown by the extract of the invention, the extract of the present invention can thus be used in the treatment of tumour pathologies resistant to treatment with chemotherapeutic agents that do not inhibit STAT3. A non-limiting example of chemotherapeutic agents that do not inhibit STAT3 is represented by the chemotherapeutic drugs used for mesothelioma, which is a tumour with pSTAT3 constitutively activated and highly chemo-resistant. Examples of the agents commonly used include pemetrexed, which is an inhibitor of thymidylate synthase; methotrexate, which is a competitive and reversible inhibitor of dihydrofolate reductase; gemcitabine, which inhibits the synthesis of DNA as a false substrate in the biosynthetic pathways of the pyrimidine nucleotides; vinorelbine, which is an antimitotic drug that binds to the monomers of tubulin, inhibiting the formation of microtubules; cisplatinum, which is an agent able to interfere with all the phases of the cell cycle binding to the DNA by means of the formation of interfilament and intrafilament cross-links in the DNA.

The experimental data presented below and in the figures obtained on tumour cell lines in which the constitutive activation of STAT3 is known also show that the extract of Cynara spp. according to the invention may be associated advantageously with one or more anti-tumour drugs, thus increasing, also synergically, the anti-tumour efficacy of the drugs themselves.

Thus, in accordance with an embodiment of the present invention, the extract of Cynara spp. as described here can be used in the prevention and/or in the treatment of an inflammatory and/or pre-tumour and/or tumour pathological condition characterised by a constitutive or anomalous activation of the STAT3 transcription factor, in association with one or more compounds having anti-tumour activity and/or one or more compounds having anti-inflammatory action.

In accordance with an embodiment, the compound having anti-tumour activity can be a chemotherapeutic agent and can be selected from the group comprising cisplatinum, doxorubicin, pemetrexed, methotrexate, vinorelbine, gemcitabine and taxol.

The present invention thus comprises the use of extract of Cynara spp. as defined here in association with one or more chemotherapeutic agents for the prevention and/or the treatment of tumour or pre-tumour pathological states characterised by a constitutive or anomalous activation of STAT3.

The association with one or more chemotherapeutic agents may be a concomitant or sequential association, or the extract and the chemotherapeutic agents can be administered at the same time (in a single administration or in separate administrations) or over a period of time of a few minutes, or can be administered sequentially or at different times, separated from one another by more than a few minutes, over the course of the day or the period of therapeutic treatment.

The administration regime will be determined by the treating doctor in accordance with the sex, the age, the state of disease, the weight and the history of the patient.

Both alone and in association, as described above, the treatment can be preventative, for example in known cases of infection so as to have possible tumourigenic effects such as those indicated above, or in the case of ablation of tumours so as to prevent said tumours from reforming.

The extract according to the present invention can be formulated in compositions that can be used for the same objectives as described above.

The present invention therefore further relates to a composition comprising, as active ingredient, an extract of *Cynara* spp. and a carrier and/or diluent and/or excipient for use in the prevention and/or in the treatment of an inflammatory and/or pre-tumour and/or tumour pathological condition characterised by a constitutive or anomalous activation of the STAT3 transcription factor.

As indicated above, the extract of artichoke or *Cynara* spp. for the purposes of the present invention can be a plant extract belonging to the *Cynara* (*Cynara* spp.) genus in accordance with the examples and the definitions provided above.

The composition may comprise, as active ingredient, an extract as defined above in the form of lyophilised extract, a dry extract or a fluid extract. As already indicated, the extract can be obtained by extraction of the leaves of artichoke or of the flower-heads of artichoke or of mixtures of the aforementioned parts, whether fresh or dried. The extraction can be performed by means of percolation-digestion, keeping the temperature controlled at 50° C., the solvent of extraction is represented for example by water, 96% ethanol, methanol, acetone, isopropanol, either as such or in mixture. The fluid extract obtained can then be subjected to evaporation, and subsequent lyophilisation or desiccation provides the lyophilised extract or the dry extract. In accordance with the present invention, the composition as defined above can be used for the prevention and/or the treatment of pathologies characterised by a constitutive or anomalous activation of the STAT3 transcription factor.

Such diseases can be, for example and as noted in the literature, inflammatory and/or pre-tumour and/or tumour diseases. The definition of the various pathological states for which the composition of the invention can be used is the same as that specified above in relation to the therapeutic use of the extract of the invention.

For the purposes of the present invention, the composition can treat pathological states characterised by a constitutive or anomalous activation of the STAT3 transcription factor as already defined above, tumour pathological states as already defined above characterised by a constitutive or anomalous activation of STAT3, and pre-tumour pathological states in which a constitutive or anomalous activation of STAT3 is present as already illustrated beforehand within the scope of the present description.

In accordance with a non-limiting example of the present invention, the composition as defined here can be used for the prevention and/or the treatment of any one of the pathological states characterised by a constitutive or anomalous activation of STAT3 listed in Table 1 above.

In addition, in accordance with a further embodiment, the composition of the invention as described here may further comprise, as active ingredients, one or more anti-tumour agents and/or one or more anti-inflammatory agents.

The present invention therefore further relates to a composition comprising, as active ingredients, extract of *Cynara* spp. and one or more compounds having anti-tumour and/or anti-inflammatory activity for use in the prevention and/or in the treatment of an inflammatory and/or pre-tumour and/or tumour pathological condition characterised by a constitutive or anomalous activation of the STAT3 transcription factor.

In accordance with an embodiment, such compounds having anti-tumour activity may be chemotherapeutic agents selected, for example, from the group comprising cisplatinum, doxorubicin, pemetrexed, methotrexate, vinorelbine, gemcitabine and taxol.

The composition of the invention can be formulated in unit doses or in a dosable manner by the treating doctor for the purpose of also enabling therapies adapted to the individual needs of each patient.

The present invention thus includes the use of compositions comprising an extract of *Cynara* spp. as defined here, optionally in association with one or more further active ingredients having anti-tumour activity and/or one or more further active ingredients having anti-inflammatory activity for the prevention and/or the treatment of tumour and/or inflammatory and/or pre-tumour pathological states characterised by a constitutive or anomalous activation of STAT3.

Such further active ingredients may be, for example, chemotherapeutic compounds, and the pathological states may be pre-tumour or tumour pathological states.

The association with the one or more chemotherapeutic agents may be a concomitant or sequential association, or the extract and the chemotherapeutic agents can be administered at the same time (in a single administration or in separate administrations) or over a period of time of a few minutes, or can be administered sequentially or at different times, separated from one another by more than a few minutes, over the course of the day or the period of therapeutic treatment.

The administration regime will be determined by the treating doctor in accordance with the sex, the age, the state of disease, the weight and the history of the patient.

Both alone and in association, as described above, the treatment can be preventative, for example in known cases of infection so as to have possible tumourigenic effects such as those indicated above, or in the case of ablation of tumours so as to prevent said tumours from reforming.

The composition with one or more active ingredients as described above (extract of *Cynara* spp. optionally in association with one or more anti-tumour agents and/or one or more anti-inflammatory agents) may obviously comprise one or more excipients or adjuvants technically used in common pharmaceutical or cosmetic practice or in the food industry. The excipients used may belong to the category of diluents, solubilisers, disintegrators, binders, lubricants, surfactants, slip agents and anti-adherents.

If necessary, the composition may also contain flavourings, colorants and preservatives used commonly in the pharmaceutical, cosmetic and food industries.

The composition according to the invention can be prepared in accordance with techniques known to a person skilled in the art and using an extract of *Cynara* spp. as defined above, optionally one or more anti-tumour agents, and one or more excipients belonging to the above-mentioned categories.

The compositions can be in any formulation considered suitable by a person skilled in the art preparing formulations intended for oral administration (for example powders, granulates, capsules in hard or soft gelatine, tablets, syrups, drops, solutions and oral emulsions), inhalation (for example aerosols, liquid and powder sprays), topical administration (gels, ointments, emulsions, pastes, foams, anhydrous solid forms for topical application, and patches) and parenterally in accordance with the techniques currently used and known to a person skilled in the art (for example for subcutaneous use, intramuscular use, intravenous use or intradermal use). In all formulations, the use of technological excipients or adjuvants is determined by selecting the substances to be used on the basis of those used commonly in pharmaceutical practice.

In the preparation of formulations based on extract of *Cynara* spp in association or not with agents having anti-tumour activity, a person skilled in the art could use any of the excipients deemed useful in accordance with the prior art in order to obtain a stable preparation suitable for use in therapy. By way of example, in the category of diluents, it is possible to use diluents in solid formulations, such as sugars, polyalcohols (for example lactose, manitol, sorbitol), cellulose, salts of inorganic acids (for example dibasic calcium phosphate), salts of organic acids including citrates, carbonate and bicarbonate titrates in the form of salts of sodium, potassium and calcium, or diluents in liquid forms, such as water, edible oils for oral use (sunflower oil, olive oil, corn oil, sweet almond oil, nut oil) or used in topical formulations (jojoba oil, short-chain, medium-chain or long-chain triglycerides), polyalcohols (glycerine, propylene glycols, hexylene glycol).

In the category of the disintegrators, it is possible to use, for example, natural or modified starches (corn starch, rice starch, potato starch), croscaramellose sodium, glycolate sodium starch, crospovidone; possible binders that can be used include natural products of the rubber type (guar gum, xanthan gum, gum arabic), sucrose and synthesis products, including polyvinyl pyrrolidone and semi-synthetic derivatives of cellulose.

The use of stearic acid and salts thereof, including the salt of magnesium, polymers of ethylene glycol, triglycerides and natural or synthetic waxes as lubricants has proven to be effective.

The surfactants are used to make one or more active ingredients contained in the formulations forming the basis of the invention more soluble or washable with water, these active ingredient acting alone or carried by one or more diluents. For example, sorbitan esters, sorbitan polyoxyethylene esters, sucrose esters and sodium lauryl sulphate can be cited.

The slip agents may be selected for example from colloidal silica, precipitated silica, whereas the anti-adherents that can be used include, for example, talc or starch.

In the preparation of injectable formulations, it is possible to choose those excipients that allow effective solubilisation or dispersion of the active substance(s). By way of example, together with water, other hydrosoluble carriers such as polyalcohols and salts of organic or inorganic acids can be used for the purpose of obtaining pH and osmolarity suitable for the administration by means of injections.

In particular cases, it will be possible to use non-hydrosoluble carriers, such as oils, or substances of synthesis commonly approved for injective use.

A person skilled in the art can prepare all the formulations using the common preparation schemas known to him.

Merely by way of example, a formulation in capsules can be prepared conveniently by grinding beforehand the extract of *Cynara* spp., mixing in a common mixer the powder obtained together with one or more anti-tumour agents and the excipients selected to prepare the formulation, for example a diluent, a disintegrator, a lubricant and a slip agent selected from those mentioned above or available on the market and approved for oral use.

In the case of a tablet, it could be necessary to granulate some or all of the mixture with a binding agent dissolved beforehand in water or introduced in mixture and using the water as an adjuvant of the process of granulation in accordance with the prior art.

The granulate may be dried, sieved and further mixed with other powders for the purpose of obtaining a mixture suitable for obtaining tablets in accordance with that known to a person skilled in the art.

In the case of parenteral use, the composition may also be provided with the active ingredients in separate containers conveniently miscible in accordance with specific operational requirements.

For the purpose of facilitating the use of the compositions described here, these can be presented in the form of unit doses containing one of the active ingredients described here (extract of *Cynara* spp. and optionally one or more anti-tumour agents and/or one or more anti-inflammatory agents) effective for a preventative and/or therapeutic use of a particular pathological condition characterised by a constitutive or anomalous activation of the STAT3 transcription factor.

The present invention further relates to a kit for the concomitant or sequential administration of an extract of *Cynara* spp. and one or more compounds having anti-tumour activity and/or one or more compounds having anti-inflammatory activity for use in the prevention and/or in the treatment of an inflammatory and/or pre-tumour and/or tumour pathological condition characterised by a constitutive or anomalous activation of the STAT3 transcription factor, said kit comprising one or more aliquots of an extract of *Cynara* spp. as defined in the present description, and one or more aliquots of one or more compounds having anti-tumour activity and/or one or more aliquots of one or more compounds having anti-inflammatory activity.

Alternatively, the kit may comprise one or more aliquots of the composition containing, as active ingredient, an extract of *Cynara* spp. as defined in the present description and one or more aliquots of one or more compounds having anti-tumour activity and/or one or more aliquots of one or more compounds having anti-inflammatory activity.

As described above, such compounds can be chemotherapeutic agents selected for example from the group comprising cisplatinum, doxorubicin, pemetrexed, methotrexate, vinorelbine, gemcitabine and taxol.

The pathologies that can be treated or prevented using the kit or using the composition of the present invention are those already indicated in the description above, pathological states characterised by a constitutive or anomalous activation of the STAT3 transcription factor that can be caused for example by viral infections (as noted in the literature), including infections by *H. pylori*, infections by the Hepatitis B virus, infections by HPV (human papilloma virus), infections by the Epstein-Barr virus (as reported in Yu et al 2009), or tumour pathological states that can be represented by any tumour characterised by a constitutive or anomalous activation of STAT3 reported in the prior art.

A non-limiting example of such tumours comprises:

prostate cancer, multiple myeloma, leukaemia, lymphoma, melanoma, carcinoma of the ovaries, carcinoma of the kidney cells, pancreatic adenocarcinoma, lung cancer, brain cancer, erythroleukaemia, squamous-cell carcinoma of the head and neck, colon cancer, mesothelioma.

More specifically, said brain tumour could be, for example, a glioma, a brain meningioma, a medulloblastoma, said lymphoma could be Sezary syndrome, EBV-associated Burkitt lymphoma, Samiri HSV-dependent lymphoma, cutaneous T-cell related lymphoma; said leukaemias may be HTLV-I-dependent leukaemia, chronic lymphocytic leukaemia (CLL), acute myelogenous leukaemia (AML), megakaryocytic leukaemia, large granular lymphocytic leukaemia (LGL).

The pre-tumour pathological states in which a constitutive or anomalous activation of STAT3 is present can be either pathological states following the ablation of a tumour, and thus pre-tumour in the sense that the tumour could reform, or pathological states in which there is a transfer from inflammation to the acquisition of malignant characteristics on the part of the cell, as reported in the literature.

Lastly, the present description also concerns a therapeutic method for the prevention and/or the treatment of an inflammatory and/or pre-tumour and/or tumour pathological condition characterised by a constitutive or anomalous activation of the STAT3 transcription factor comprising the step of administering to an individual in need of it a therapeutically active quantity of extract of Cynara spp. or of a pharmaceutical composition comprising extract of Cynara spp. optionally in association with one or more anti-tumour and/or anti-inflammatory compounds.

The method forming the basis of the present invention can be carried out by administering to a subject who presents an inflammatory and/or pre-tumour and/or tumour pathological condition characterised by a constitutive or anomalous activation of the STAT3 transcription factor, therapeutically effective doses of the extract as defined here, optionally in association with one or more anti-tumour or anti-inflammatory drugs; or by administering therapeutically effective doses of the composition as defined here, optionally further comprising one or more anti-tumour and/or anti-inflammatory drugs, or by administering the extract and one or more anti-tumour and/or anti-inflammatory drugs using the kit as defined here.

The administration as described above can be performed concomitantly or sequentially in accordance with the administration regime selected by the doctor.

Numerous experimental data have been reported that demonstrate the efficacy of the extract according to the present invention.

USED CELL LINES

L428 Human lymphoma cell line. Available from DSMZ ACC197

KARPAS Human lymphoma cell line with constitutively activated STAT3. Available from Cell Bank Australia #6072604

Human T-cell lymphoma cell line, established from peripheral blood of a human of 25 years of age with non-Hodgkin T-cell lymphoma cells in 1986, now classified as lymphoblastoid lymphoma cell line. Karpas 299 expresses Stat3 phosphorylated in tyrosine 705 and serine 727.

MSTO211H Human lung biphase mesothelioma cell line with constitutively activated STAT3. Available from ATCC #CLR-2081

Human mesothelioma cell line, established from the pleural spill of a human of 62 years of age with mesothelioma (biphase malignant) who had not had any prior therapy. Cell line MSTO211H expresses high levels of pStat3). (Tsao et al. Inhibition of c-Src expression and activation in malignant pleural mesothelioma tissues leads to apoptosis, cell cycle arrest, and decreased migration and invasion. Mol Cancer Ther 2007; 6:1962-1972.)

DU-145 Human carcinoma cell line available from ATCC #HTB-81

The cell line DU145 is a human prostate cancel cell line of moderate metastatic potential compared with PC3 cells, which have high metastatic potential. The DU145 cells are not hormone-sensitive and do not express PSA (prostate-specific antigen). The cell line DU145 expresses pStat3 in a constitutive manner.

HCT116 Human colon cancer cell line available from. Available from ATCC #CCL-247.

MDA-MB-231 Human mammary adenocarcinoma cell line. Available from ATCC #HTB-26.

NCI-h28 Human stage-4 mesothelioma cell line. Available from ATCC#CRL-5820

MPP-89 Human mesothelioma cell line. Available from CABRI, access number ICLC HTL00012

The following examples show how the extract of cynara scolymus of the present invention is able to:

reduce the vitality in mesothelioma cells (MSTO211H, MPP-89, NCI-H2052, NCI-H28) in a dose-dependent manner, acting less strongly on non-transformed mesothelial cells (HMC);

reduce the ability to form colonies in assays of clonogenic survival over the same cell lines, induce cell death of malignant mesothelioma cells MM in apoptotic assays;

inhibit the migration and the proliferation of MM cells in wound healing assays;

sensitise the MM cells with successive treatments with a chemotherapeutic agent, such as pemetrexed;

induce damage in the DNA of MM cells whilst not inducing damage to the DNA of HMC cells;

reduce the ability tumour transplantation with MSTO cells on cells pre-treated with the extract;

have a dose-dependent effect in the treatment of xeno-transplantation of MSTO.

EXAMPLES

1. Analysis of the Phosphorylation of STAT3 by Means of Western Blot. Results Reported in FIGS. 1-3.

1.1. Cell Lysis and Western Blotting.

The cells were lysed in ice for 30 min in lysis buffer NP40 (50 mM Tris-HCl pH 7.4, 150 mM NaCl, 1% NP-40, 1 mM EGTA, 1 mM EDTA) complemented with inhibitors of protease and phosphatase (5 mM PMSF, 3 mM NaF, 1 mM DTT, 1 mM NaVO4). Equal amounts of total extracts of protein (30 µg) were broken down by means of denaturing electrophoresis (SDS-PAGE) in 8% polyacrylamide gel and transferred for 2 hours on nitrocellulose membrane. The membranes were blocked with a 5% solution of milk dissolved in TBS-Tween_20 0.05% for 1 hour and incubated with the specific primary antibodies. The following primary antibodies were used: anti-beta actin (A-2228, SIGMA), anti-pSTAT3 (Tyr-705) (sc8059, Santa Cruz) and anti-STAT3 (sc7179, Santa Cruz). The secondary antibodies were peroxidase-conjugated (Santa Cruz), and ECL reagents (Amersham, GE Healthcare. Piscataway, N.J., USA) were used for the chemiluminescence.

1.2. Treatment of the Cell Lines of MPMs and of Normal Commercial Mesothelial Cells (HMC) with Extract of Cynara scolymus.

The cell lines of MPMs (MSTO-211H, NCI-H28, NCI-H2052, MPP89) were acquired from ATCC (Rockville, Md.)

whilst the HMCs (Human Mesothelial Cells) were acquired from Tebu-Bio (France). All the lines were grown in monolayers at 37° C. and at 5% of CO2 in specific culture media. The artichoke extract was dissolved conveniently in a solution of water for injectable solutions and ethanol in a ratio of 1:1 at an initial concentration of 30 mg/ml. To test the anti-tumour property, the product was then added directly in the medium of the various cell lines using various concentrations and various times, as shown in the drawings.

1.3. Results

The results, shown in FIGS. 1 to 3, show how the assayed extract inhibits the phosphorylation of STAT3 compared with the controls not treated with the extract.

FIG. 1 shows the data with the control treated with just the carrier and extract of *Cynara* spp., 100 µg/ml of culture medium for 24 hours (actina control), and FIG. 2 shows the data with cells treated for 24 hours with various concentrations of extract of *Cynara* spp.: 25 µg/ml, 50 µg/ml, 75 µg/ml.

Figure 1A:
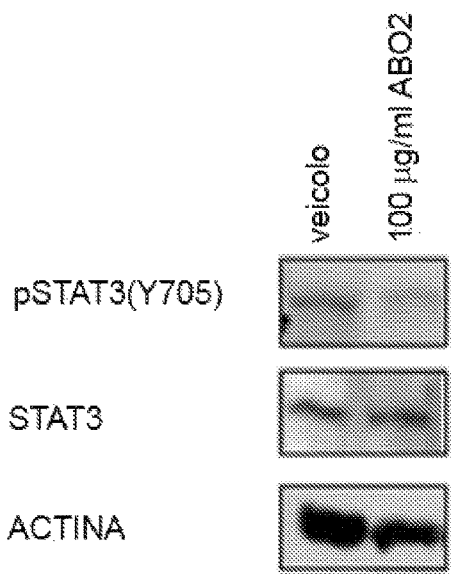
FIGS. 1 and 2 show the data obtained on MSTO211H cells treated with extract of *Cynara* spp. in accordance with the description.
Figure 1B:
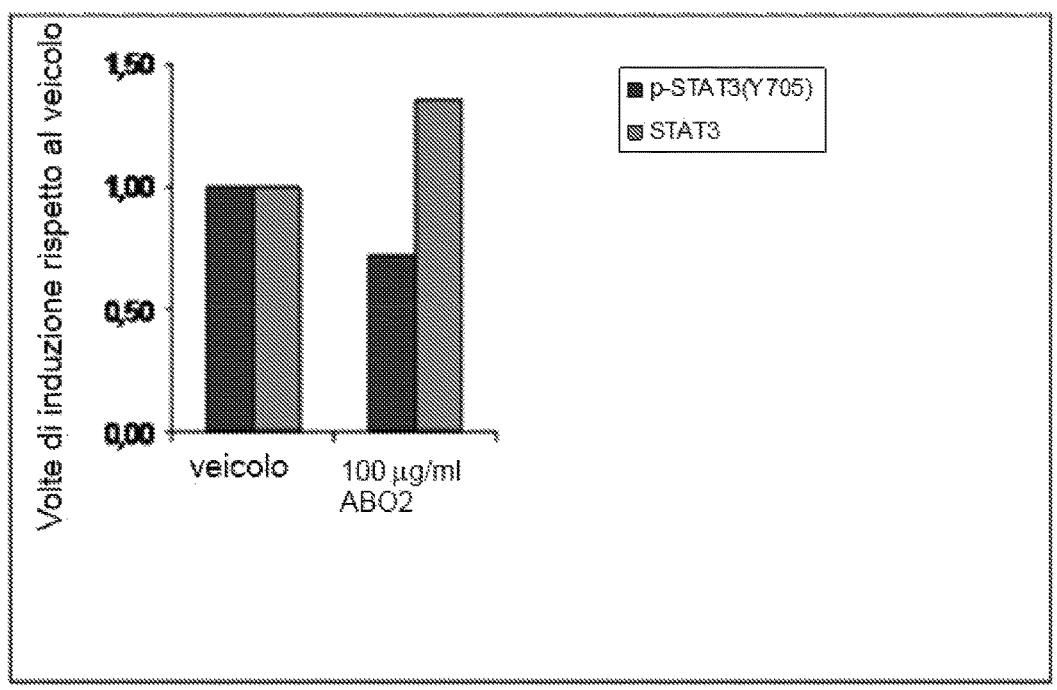
Figure 2:
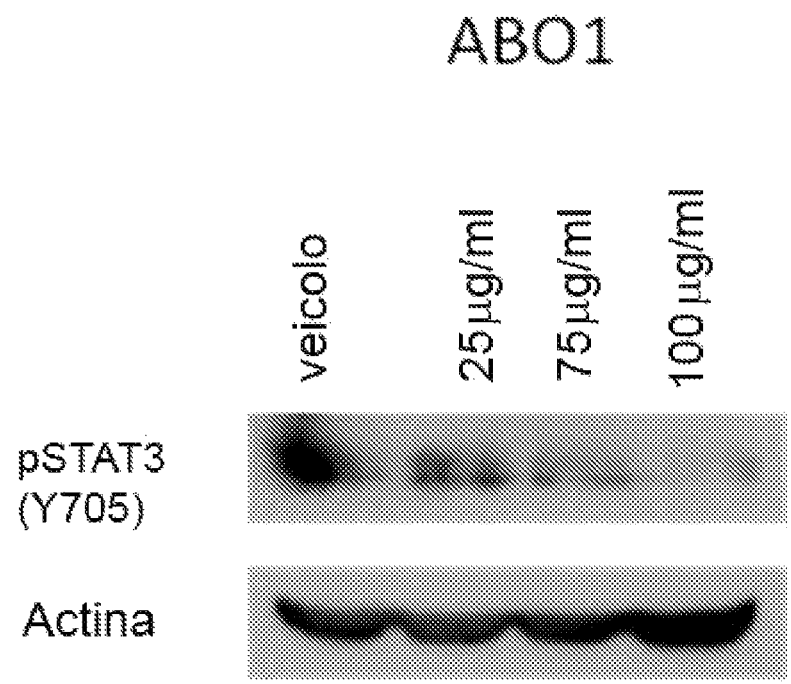
Figure 3A:
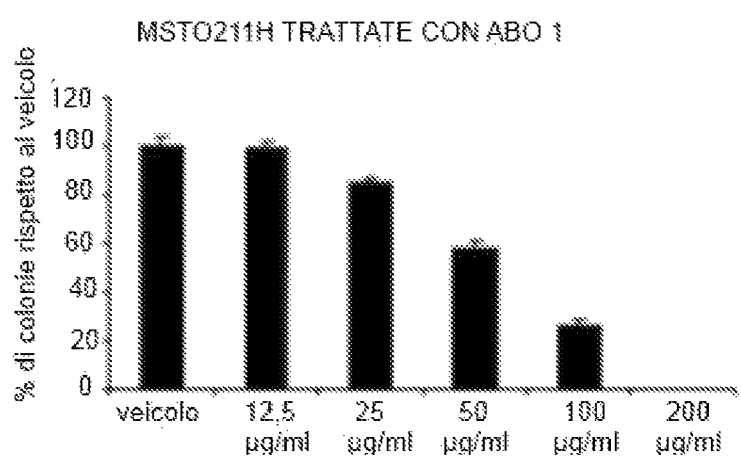
Figure 3B:
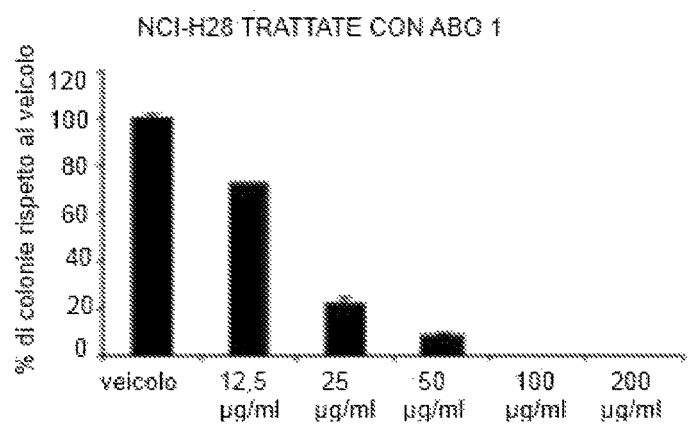
Figure 3C:
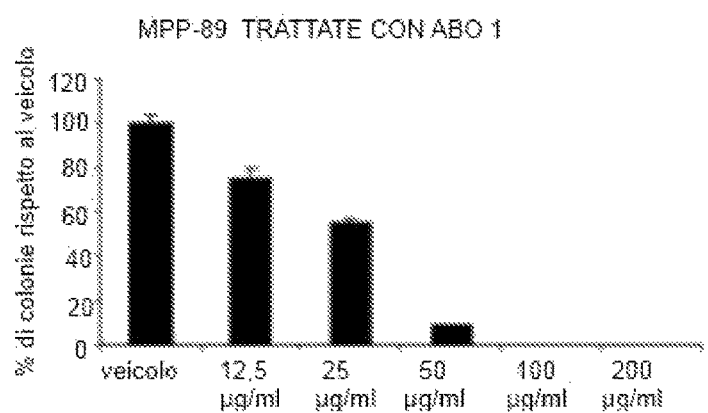
Figure 3D:
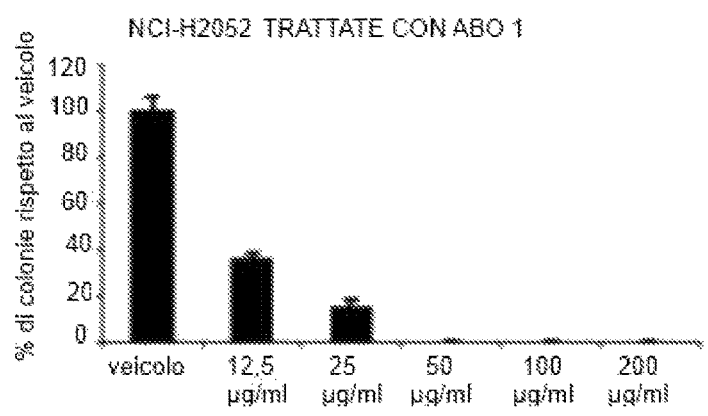

As for FIG. 1, the data with the control treated with just the carrier and extract of *Cynara* spp. are shown, 100 µg/ml of culture medium for 24 hours (actina control).

2. The Extract of *Cynara scolymus* and Cynaropicrin Inhibit the Activation of STAT3 in DU-145 Cells and in KARPAS Cells:

As can be seen in FIGS. 17-20, both the extract of *Cynara scolymus* and cynaropricrin act on STAT3. 200 µg/ml of extract that contains 0.181% of cynaropricrin contain 1.2 µM of cynaropricrin. The figures show that the effect observed with 25 µM of cynaropricrin is equal to the effect observed with 200 µg/ml of extract, with titre of cynaropricrin equal to 0.181%, that is to say comprising 1.2 µM of cynaropricrin. Since the dose of extract used contains 1.2 mM of cynaropricrin, the data obtained show that the extract is more effective than cynaropricrin.

3. Assay of Clonogenicity on Cells of Malignant Pleural Mesothelioma (MPM)

MPM cells (MSTO211H, NCI-H28; MPP-89; NCI-H2052) were seeded at 200 cells per well and were treated with various growing concentrations (control just with carrier; 12.5 µg/ml; 25 µg/ml; 50 µg/ml; 100 µg/ml, 200 µg/ml) of extract of *Cynara scolymus* in accordance with the present description. Each point was plated in duplicate in the 6-well multiwall. The colonies formed were stained with violet crystal 15-21 days later. The assay of colony formation, also known as a clonogenic assay, is a technique used to assess the efficacy of anti-tumour compounds in terms of the ability of the tumour cells to form colonies from a single cell. A colony is considered to be a group of 50 or more cells (clones) originating from a single cell.

The results of the experiment, shown in FIGS. 3a-3d, show the dose-dependent ability of the extract of the invention to inhibit, in a dose-dependent manner, the formation of colonies in all the MPM cell lines tested.

The same assay was also performed on HCT116 colon cancer cells, DU145 prostate cancer cells and MDA-MB-231 breast cancer cells. In this case too, the data shown in FIGS. 4a, b, e and c show the efficacy of inhibiting, in a dose-dependent manner, the formation of colonies from the extract of the invention.

4. ATPlite™ Cell Vitality Assay

The vitality of various cell lines following exposure to the extract of the invention at various concentrations was assessed using the ATPlite™ assay (Perkin Elmer) in accordance with the producer's instructions. Where indicated, the term "carrier" refers to a solution of water for injectable solutions and ethanol at a concentration of 1:1 used in the same volumes used for the treatments.

ATPLite™ is a system for monitoring the levels of adenosine triphosphate (ATP) based on the activity of firefly (*Photinus pyralis*) luciferase. This luminescence assay is an alternative to colorimetric, fluorometric and radioisotopic tests for the quantitative evaluation of the proliferation of cultured mammalian cells subjected to treatment with possible substances contained in the culture medium. The monitoring of ATP is used in fact to evaluate the cytostatic and anti-proliferative effects of a vast range of drugs, modifiers of the biological response, and biological compounds. The ATPLite™ test system is based on the production of light caused by the reaction with addition of ATP luciferases and D-luciferin. The light emitted is proportional to the concentration of ATP within certain limits. The quantity of ATP in cells correlates with the cell vitality.

The cell vitality of various types of MPM cell lines (MSTO211H, MPP89, NCI-H28, NCI-H2052) and of HMC cells (untransformed mesothelial cells provided by willing donors) were assayed following treatment with various concentrations of extract according to the invention (control just with carrier; 12.5 µg/ml; 25 µg/ml; 50 µg/ml; 100 µg/ml, 200 µg/ml).

Figure 5:
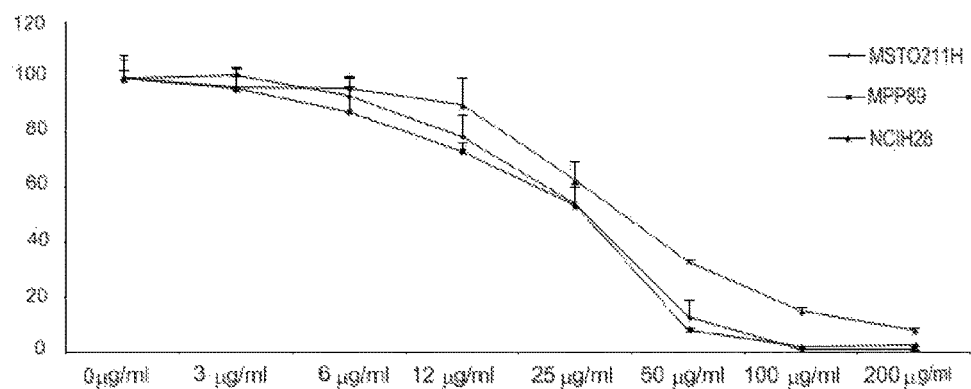

The graph in FIG. 5, which shows the results of the assay, shows that the extract is able to significantly reduce cell vitality in a dose-dependent manner.

Figure 6A:
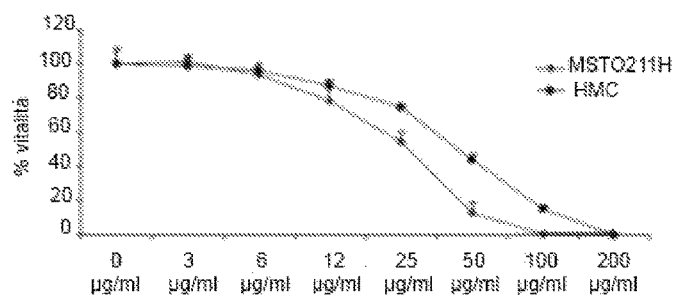
Figure 6B:
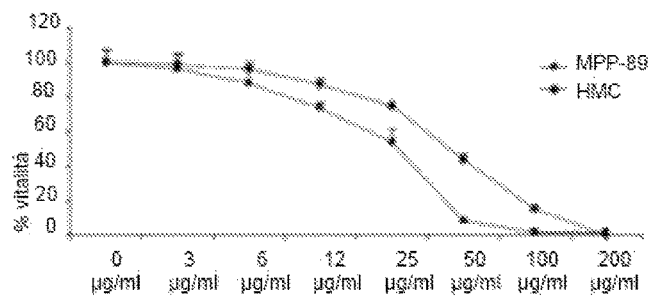
Figure 6C:
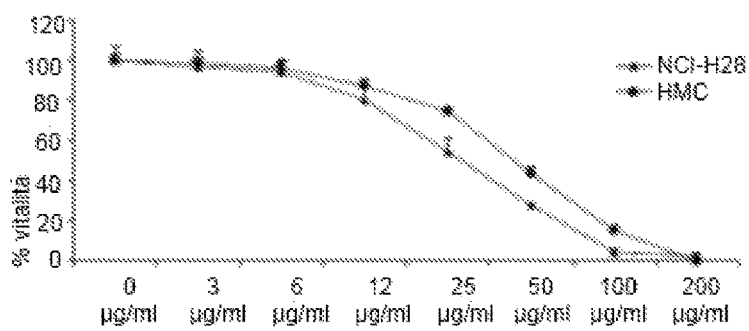

The effects on cell vitality were also tested on untransformed mesothelial cells (HMCs), towards which the extract forming the basis of the invention demonstrated lower cytotoxicity compared with the tumour lines (FIGS. 6A-6C) (FIG. 6A-6C).

5. WST Assay of Cell Vitality and Proliferation, Comparison Between the Cytotoxic Efficacy of the Extract of the Invention and Cynaropicrin.

Cytotoxicity was assayed using the WST assay (WSTs=water soluble tetrazolium salts), and utilises the ability of mitochondrial dehydrogenases to separate the tetrazole ring from the yellow-coloured WST molecule (tetrazolium salt) to give an orange formazan salt. The amount of formazan produced following the treatment of the cells with the substances being tested is measured using spectrophotometry and is proportional to the number of living cells. WST-1 and in particular WST-8 (2-(2-methoxy-4-nitrophenyl)-3-(4-nitrophenyl)-5-(2,4-disulfophenyl)-2H-tetrazolium) are advantageous with respect to MTT because they reduce outside the cells, in combination with PMS as electron mediator, to produce water-soluble formazan. Lastly, the WST assays: (1) can be read directly (in contrast with MTT, which requires a solubilisation phase), (2) and give a more effective signal than MTT, and (3) reduce the toxicity for the cells (in contrast with MTT, which produces insoluble formazan that accumulates within the cells).

Figure 9:
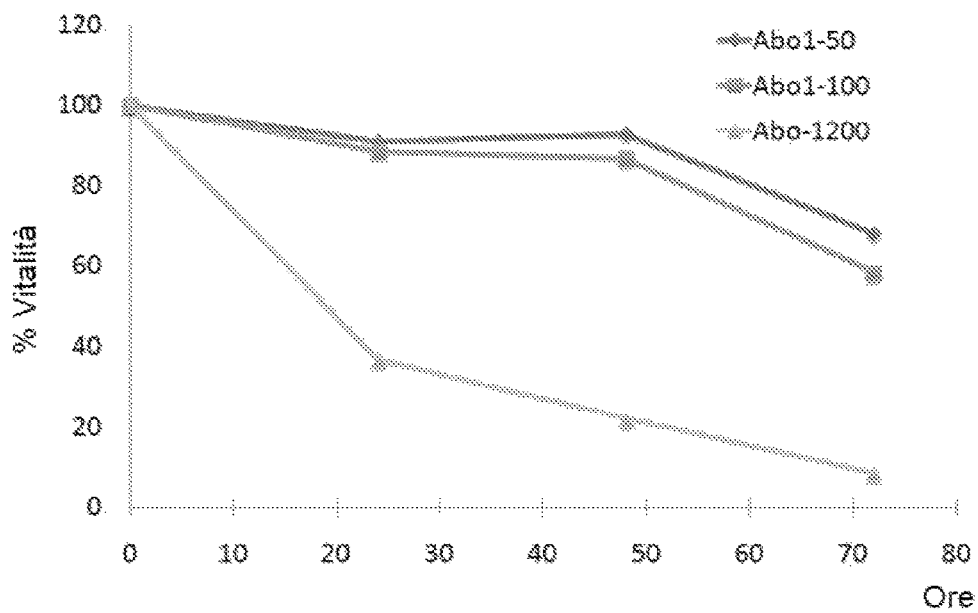

The following WST assays were performed:

6.1 WST-1 Assay on Cell Line DU145 with 50, 100 e 200 µg/Ml of Extract of *Cynara scolymus* at 24-48-72 Hours Shown in FIG. 9

Figure 7:
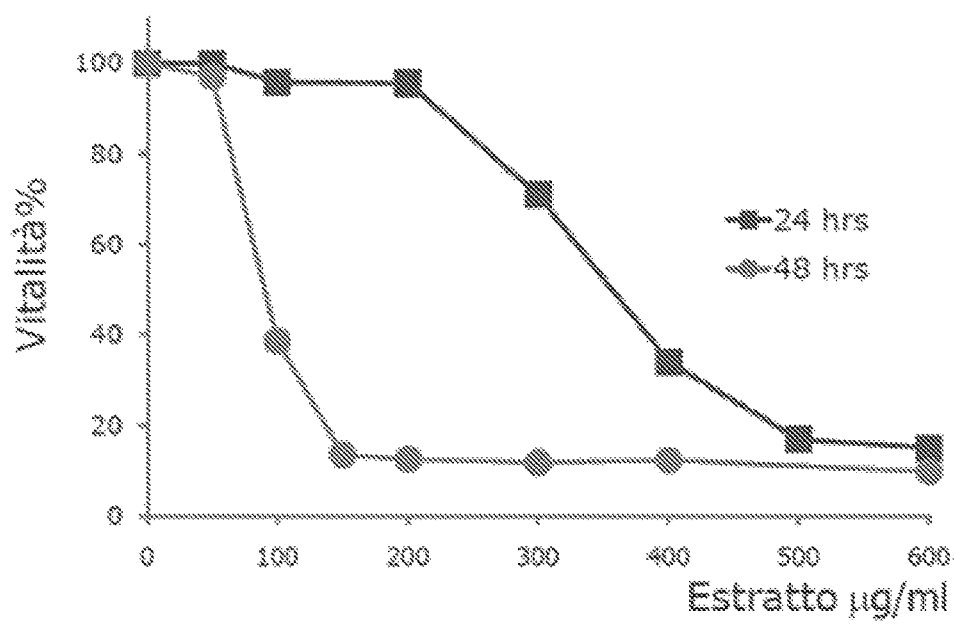

6.2 WST-1 assay on cell line DU145 at 24 and 48 hours with 0-100-200-300-400-500-600 µg/ml of extract of *Cynara scolymus* (cynaropicrin=1.361%), which inhibits, in a time-dependent and dose-dependent manner, the vitality of the DU-145 cells. FIG. 7, which shows the assay, also shows the content in cynaropicrin, expressed both in µg/ml and in µM, of the assayed extract at concentrations 100 µg/ml; 200 µg/ml; 300 µg/ml; 400 µg/ml; 500 µg/ml; 600 µg/ml (comprising, respectively, 0.47 µM; 0.94 µM; 1.41 µM; 1.88 µM; 2.35 µM and 2.82; of cynaropicrin).

6.3 WST-1 assay on cell line DU145 at 24 and 48 hours with cynaropicrin 0-10-20-30-40-50-60 µM inhibits, in a dose-dependent and time-dependent manner, the vitality of DU-145 cells. The results are shown in FIG. 8.

Figure 8:
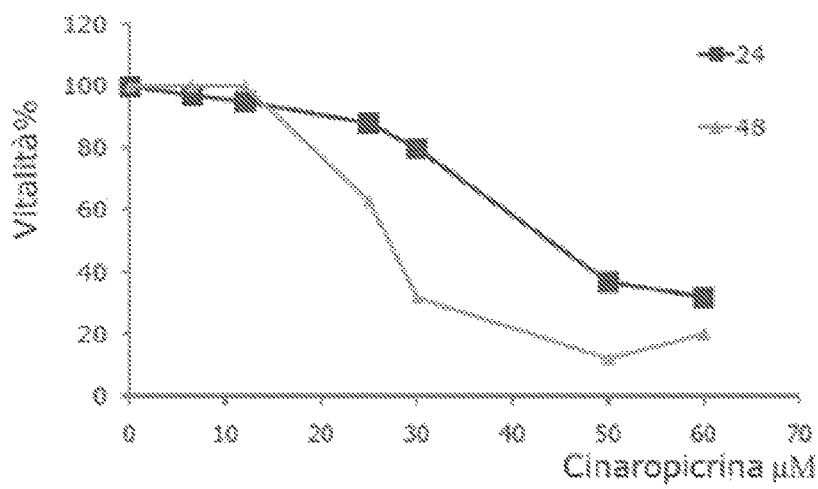

It would appear, by comparing FIGS. 7 and 8, that the assayed extract is more than 40 times more effective than cynaropicrin.

7. Assays of Cell Vitality in Co-treatment with Chemotherapeutic Agents

Cell lines MSTO211H and NCI-H2052 were used to evaluate the effects of the association of extract of *Cynara scolymus*+anti-tumour drug.

Figure 10A:
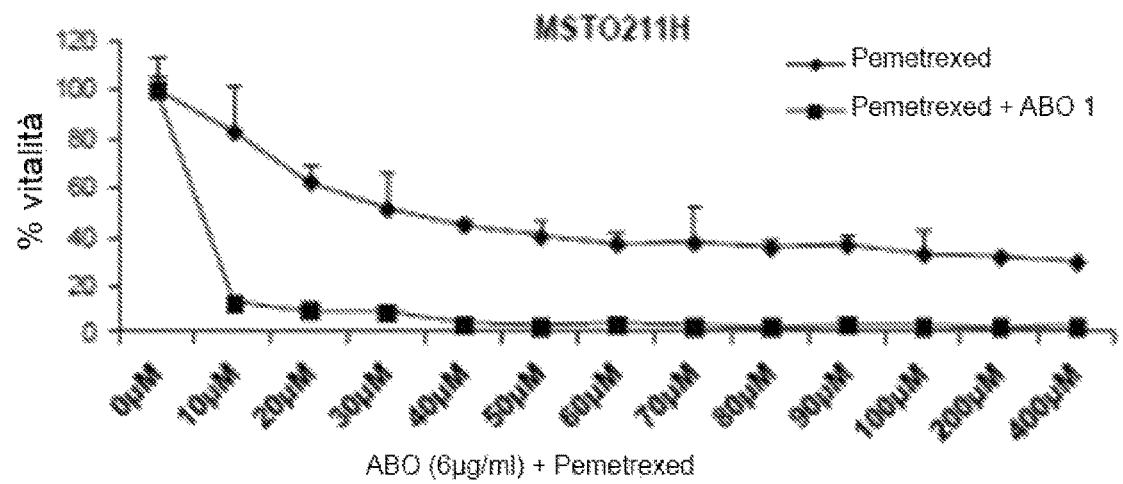
Figure 10B:
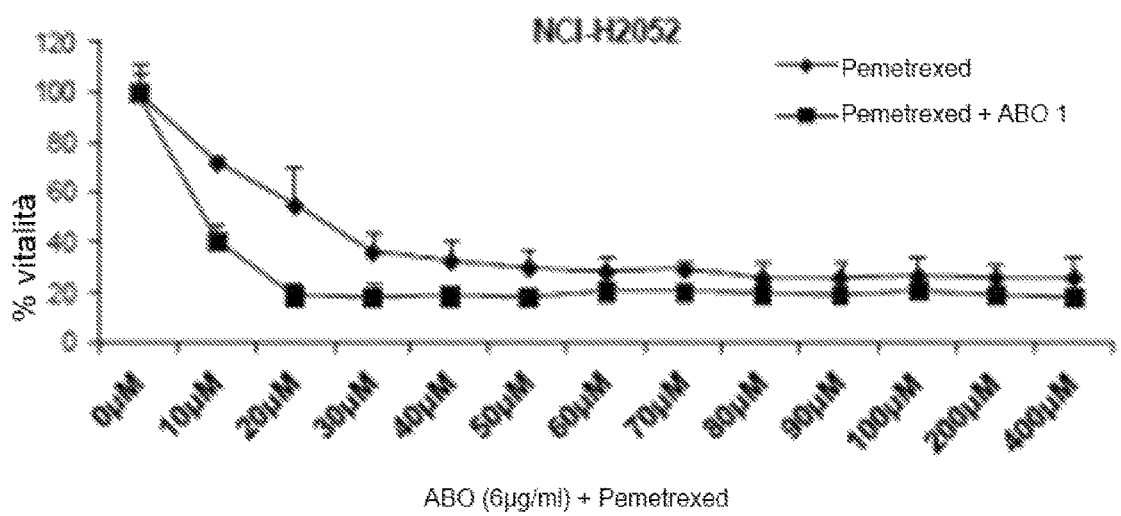
Figure 10C:
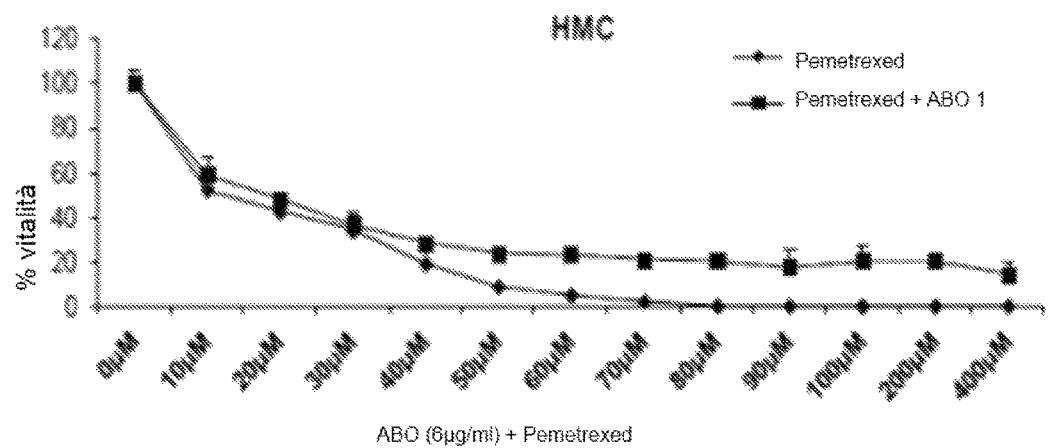

The assay shown in FIG. 10 was performed using ATPlite™ assay (Perkin Elmer) in accordance with the producer's instructions.

A solution of water for injectable solutions and ethanol at a concentration of 1:1 was used in the same volumes used for the treatments.

Reagents:

pemetrexed (Alimta, Lilly) diluted in accordance with the producer's instructions.

7.1 Association of Extract of *Cynara* spp. and Pemetrexed with ATPlite™ Assay

FIG. 10 shows the vitality curve for MSTO211H after 72 h of treatment with pemetrexed and pemetrexed in association with extract of *Cynara* spp. Graph A shows the treatment with the extract at non-cytotoxic dose (6 µg/ml) and pemetrexed for the MSTO211H cells, whereas graph B shows the treatment with the extract at non-cytotoxic dose (6 µg/ml) and with pemetrexed (various concentrations) for NCI-H2052 cells, and graph C shows the treatment with the extract at non-cytotoxic dose (6 µg/ml) and with pemetrexed (various concentrations) for untransformed HMC cells. The concentrations of the assayed compound are plotted on the abscissa, whereas the cell vitality expressed in percentage is plotted on the ordinate.

FIGS. 10A and B show how the treatment with extract sensitises the tumour lines to the treatment with pemetrexed. In the curve with double treatment, it is clear how just a concentration of pemetrexed of 10 µM is sufficient to lower the cell vitality of the tested lines. It is interesting to note that, in the non-tumour line, the extract has a protective effect towards pemetrexed.

7.2 Evaluation of Cell Vitality with WST-1 Assay

The assays were carried out in parallel with variable doses of cynaropicrin in place of the extract to compare the efficacy of the extract and that of cynaropicrin.

FIG. 10 shows the data obtained by incubating DU145 cells with cisplatinum (graph A), doxorubicin (graph B) and taxol (graph C) with just the carrier (cntr), with two different concentrations of extract of *Cynara scolymus* (abo-1) with just drug and with two different concentrations of extract of *Cynara scolymus* (abo-1) in association with the drug.

Figure 11A:
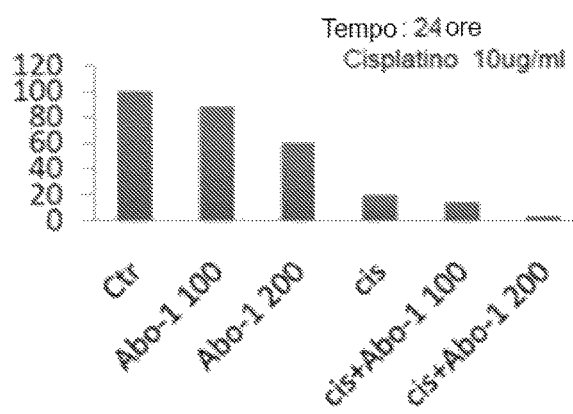
Figure 11B:
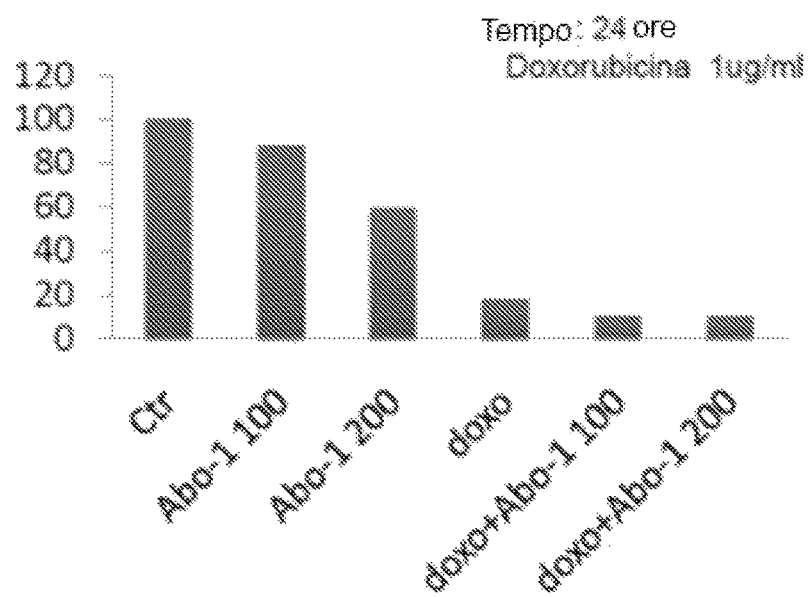
Figure 11C:
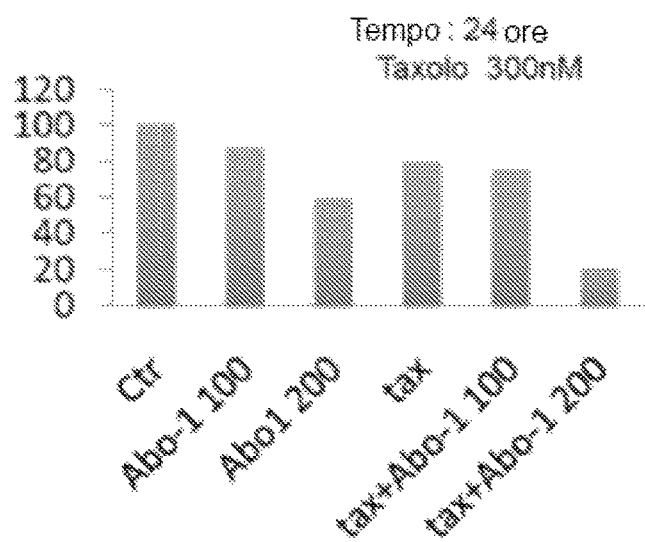

The extract used in the experiments shown in FIG. 11 had a content of 0.181% in cynaropicrin. The figure thus shows the concentrations of cynaropicrin with 100 and 200 µg/ml of extract equal respectively to 0.18 and 0.36 µg/ml of cynaropicrin.

Figure 12:
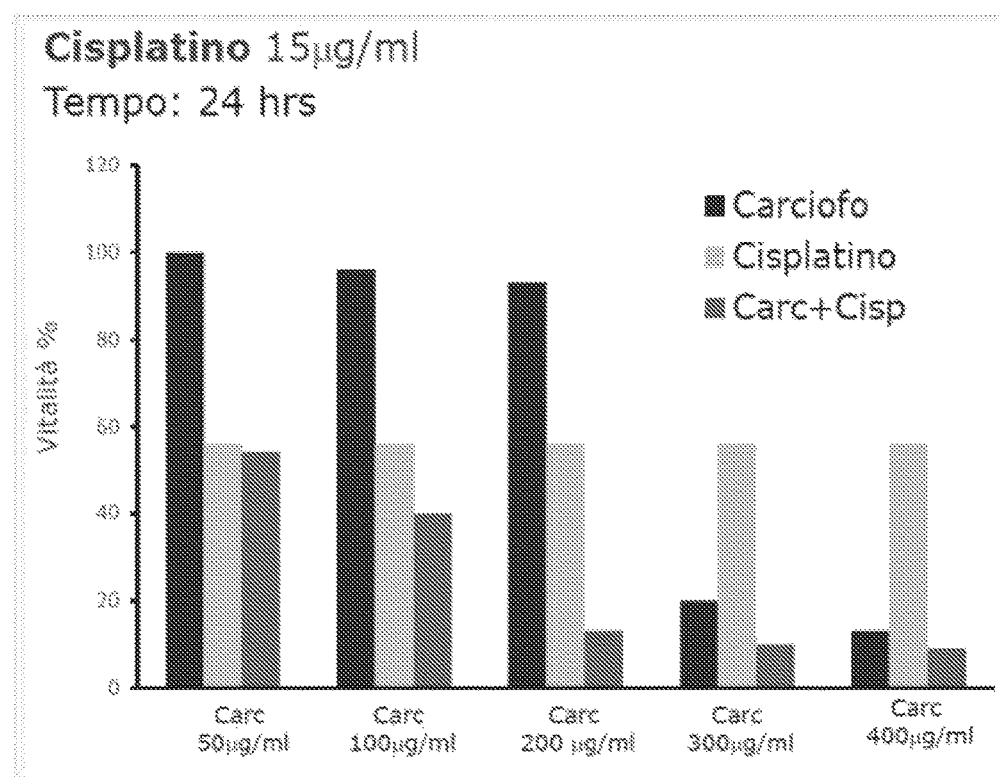

FIG. 11 shows the association between growing concentrations of extract of *Cynara Scolymus* (cynaropicrin=1.361%) and cisplatinum at fixed concentration of 15 µg/ml and FIG. 12 shows the association between extract of *Cynara Scolymus* (cynaropicrin=1.361%) and doxorubicin at fixed concentration of 2 µg/ml.

The figure also shows the values for the treatment with just extract (black) or just drug (white).

Figure 13:
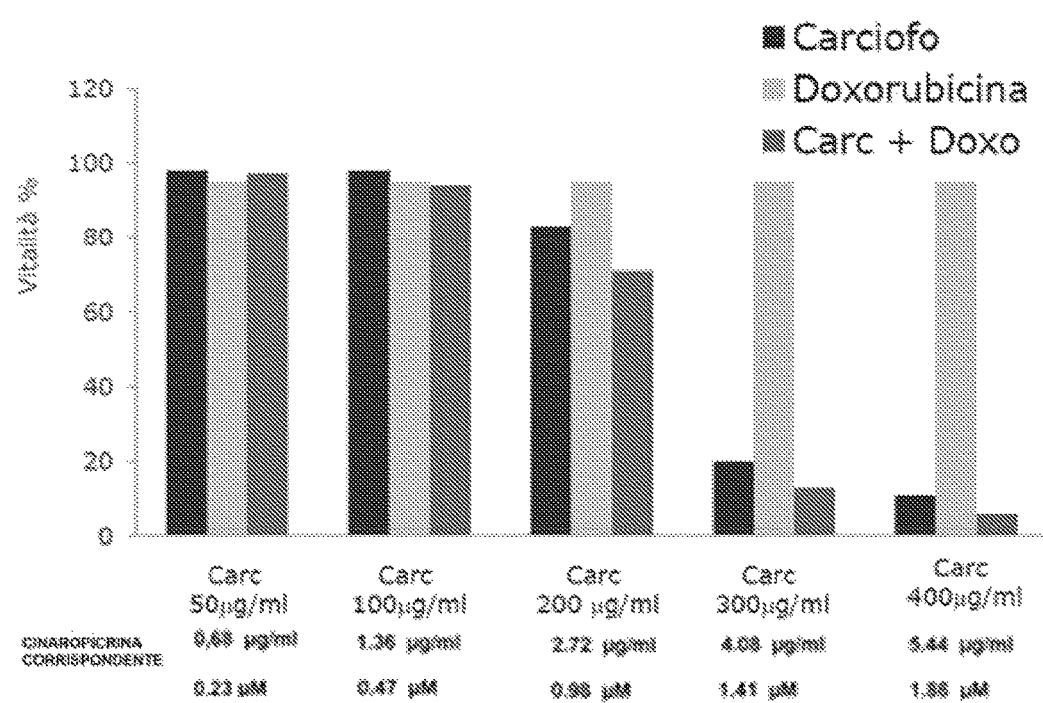
Figure 14:
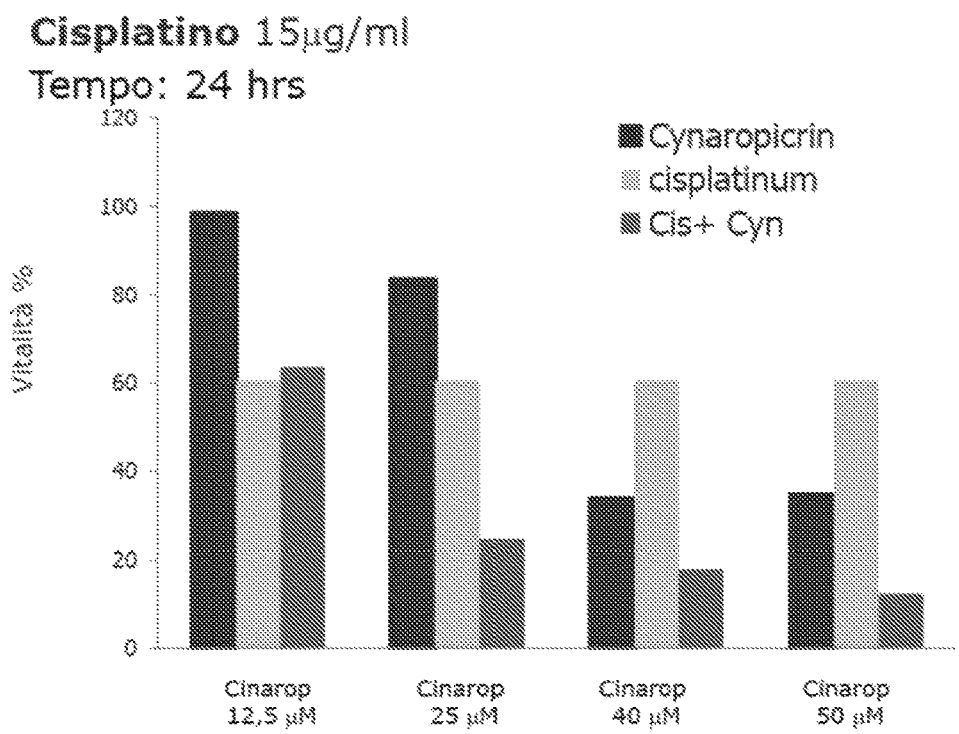
Figure 15:
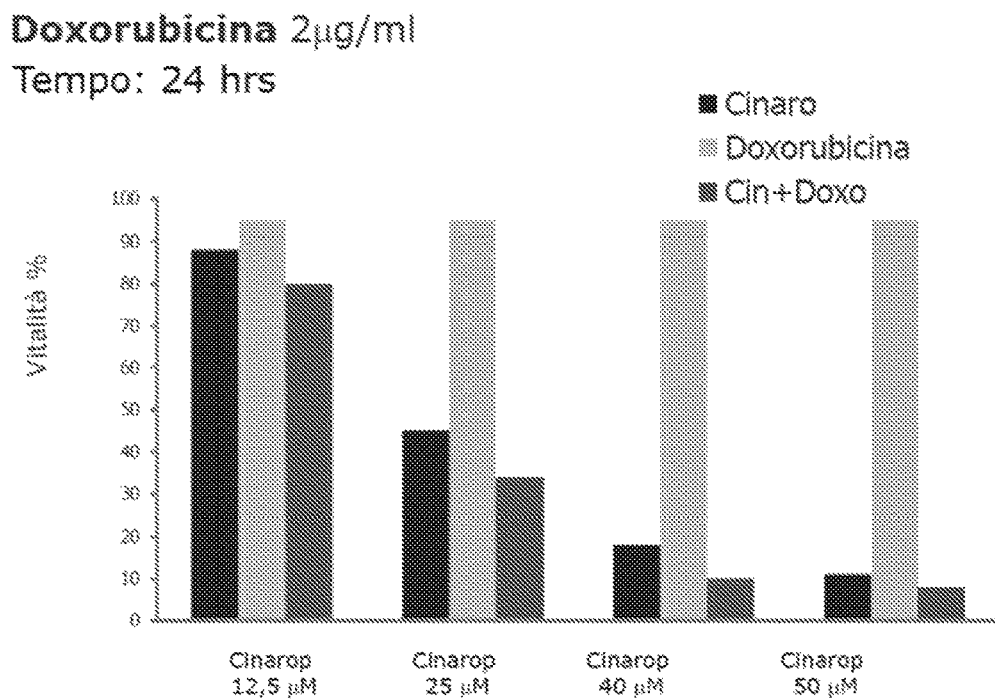

FIGS. 13 and 14, similarly to FIGS. 11 and 12, show the results of the same experiments performed with cynaropicrin in place of the extract of the invention, and show how the extract is significantly more effective than cynaropicrin.

FIG. 14 thus shows the association between cynaropicrin at growing concentrations and cisplatinum at a fixed concentration of 15 µg/ml, and FIG. 14 shows the association between cynaropicrin and doxorubicin at a fixed concentration of 2 µg/ml.

The figure also shows the values for the treatment with just cynaropicrin (black) and just drug (white).

8. Wound Healing Assay

Figure 16A:
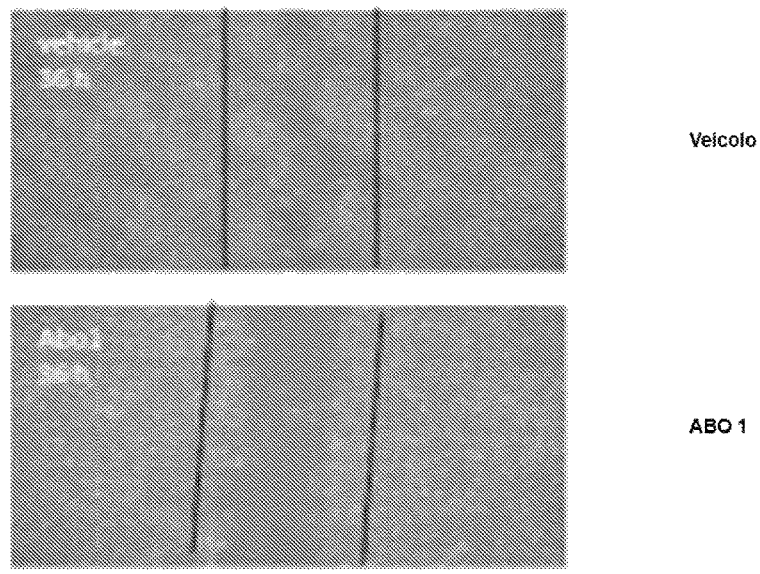
Figure 16B:
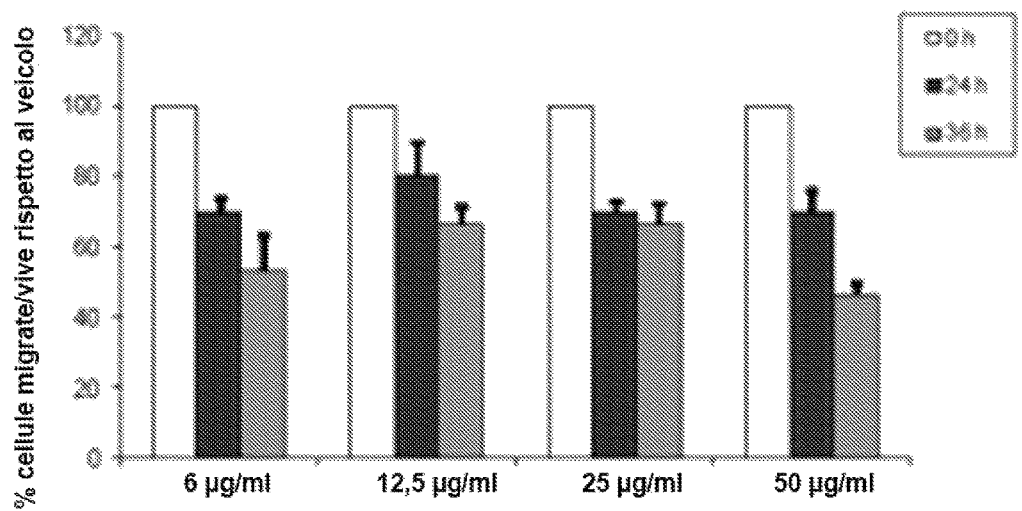
Figure 17:
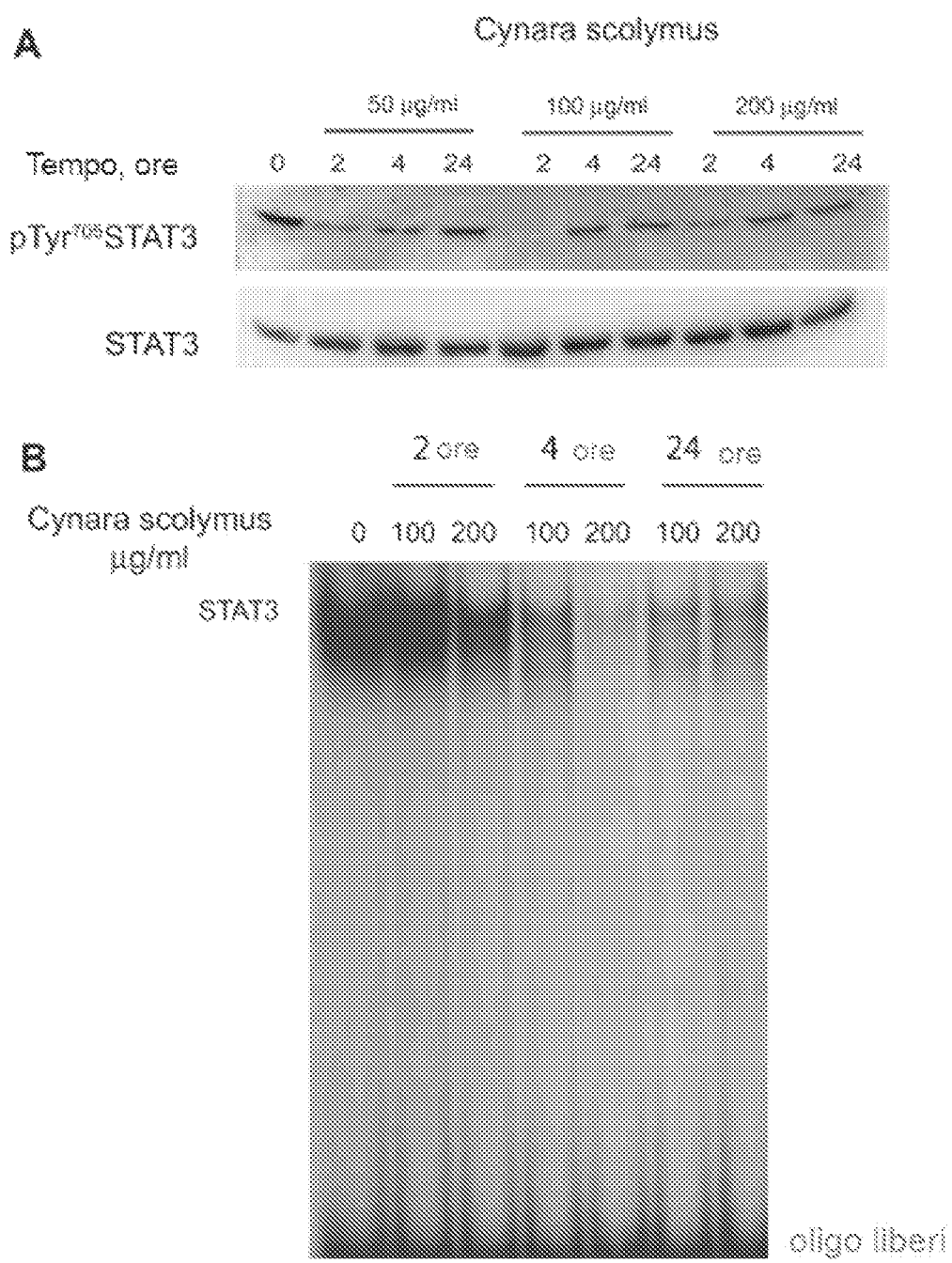
Figure 18:
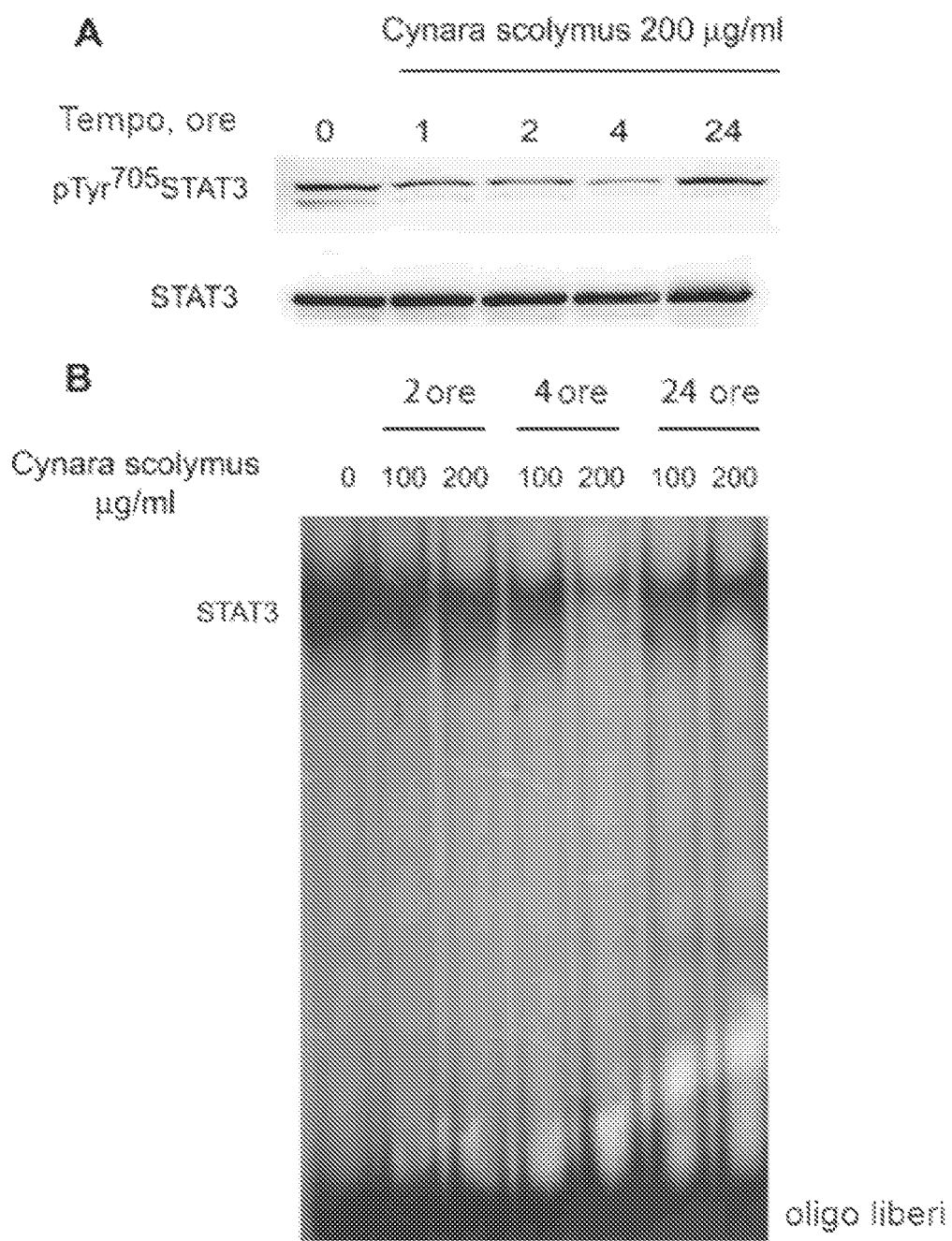
Figure 19:
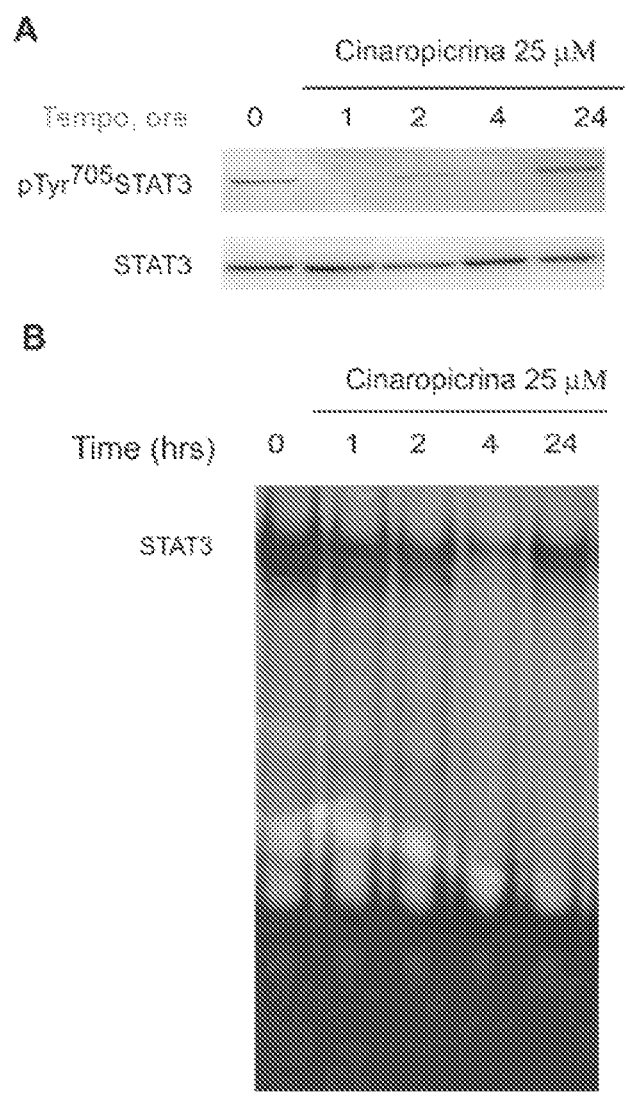
Figure 20:
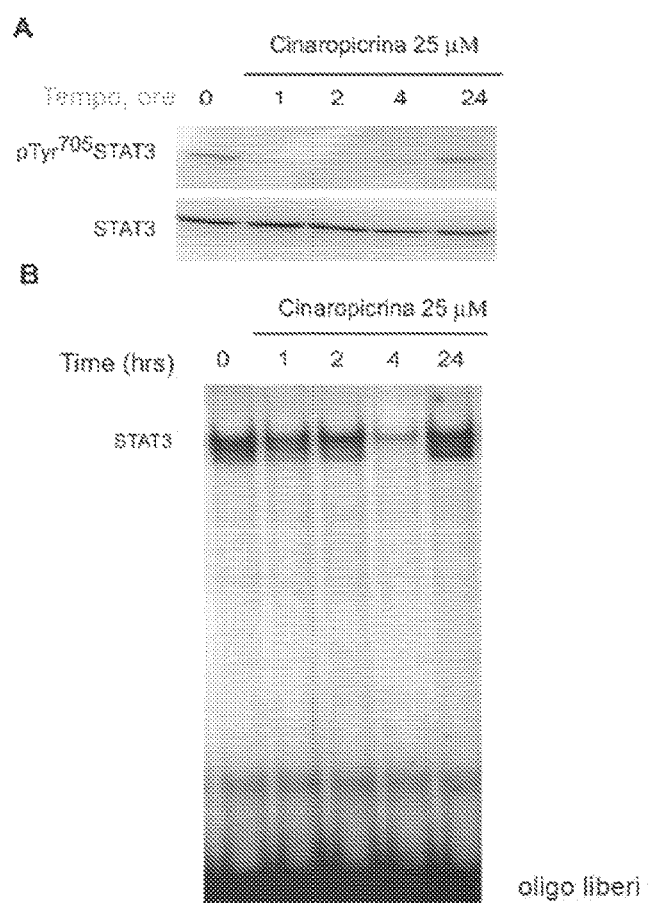
Figure 21A:
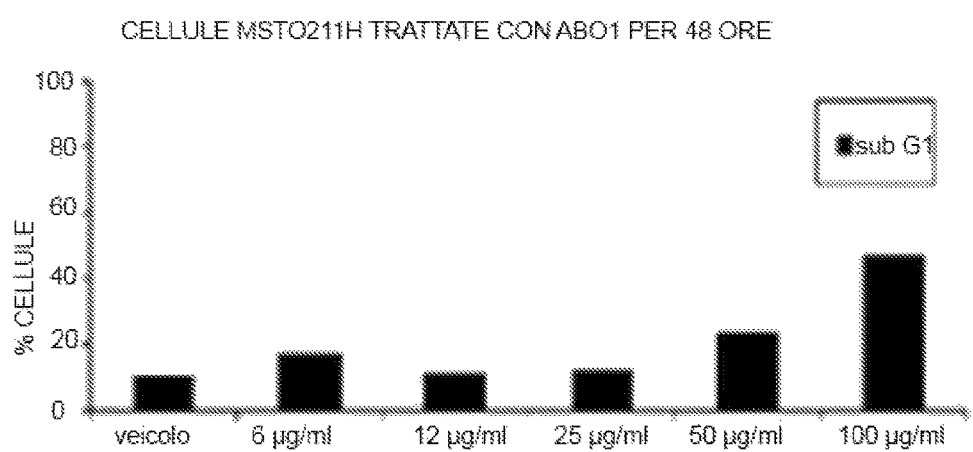
Figure 21B:
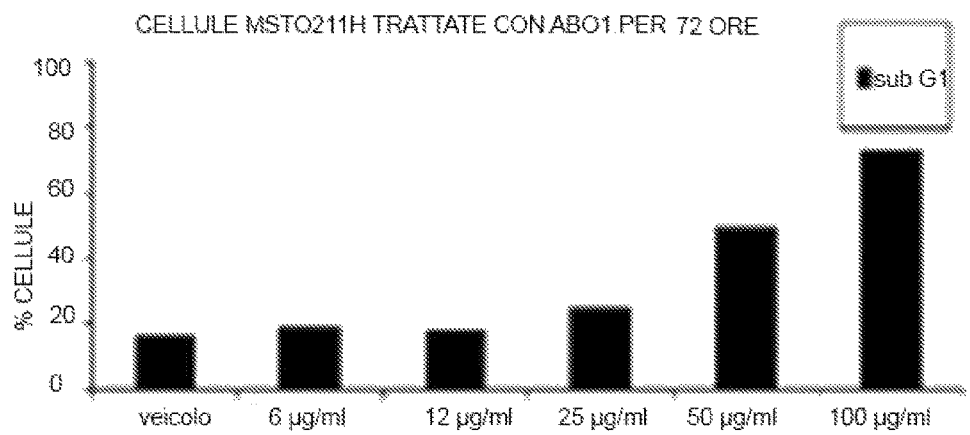
Figure 22:
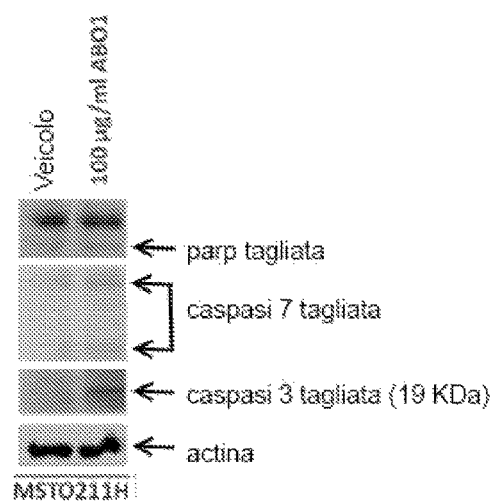
Figure 23:
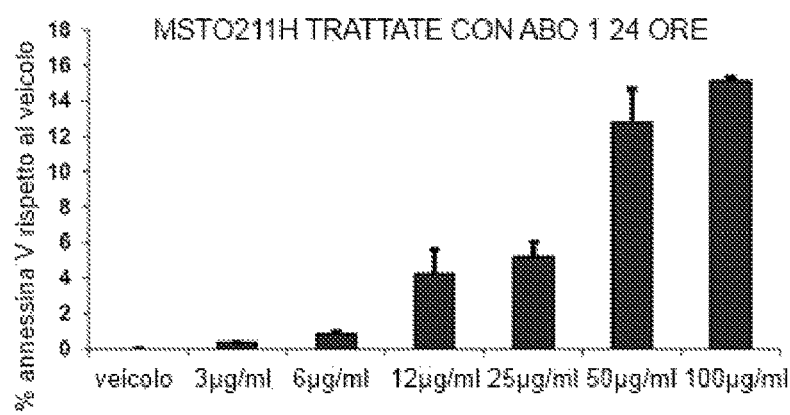

The wound healing assay (FIG. 16) is simple, inexpensive, and one of the first methods developed for studying directional cell migration in vitro. This method mimics cell migration during would healing in vivo. The basic steps involve creating a "wound" in a cell monolayer, then monitoring a specific zone of the "wound" by capturing images at the beginning and at regular intervals during the cell migration necessary to close the "wound". The MSTO211H cells cultivated with a confluency of 95% were seeded in 6-well textile plates and the "wound" (or cut) was made with a puncture by 10-microlitre sterile pipette to remove the cells. Digital micrographs were produced after the wounds at the indicated times. The final bar chart shows the efficacy of closure of the cut (quantification number of the cells in %) treated with carrier or ABO 1 at the indicated times.

9. Assay to Assess the Induction of Apoptosis

Figure 26:
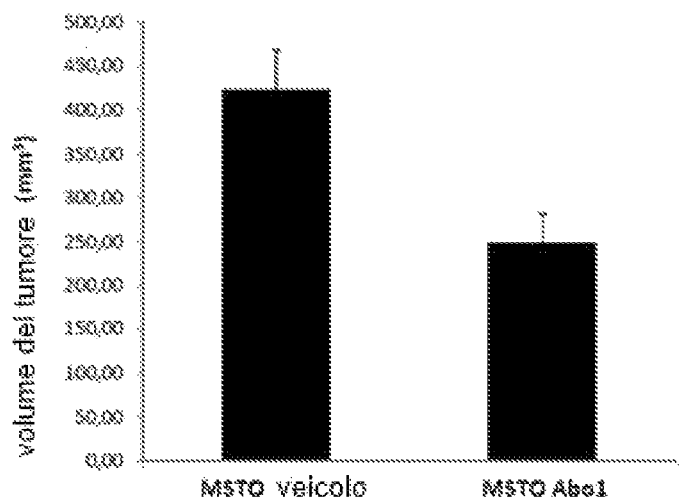
Figure 27:
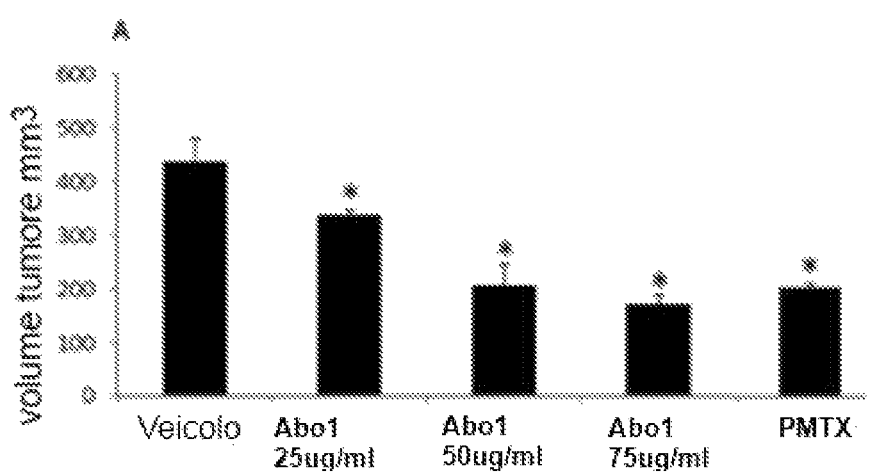

See FIGS. 26-27)

9.1 Western Blotting

The same technique as described in point 1.1 was used, and the following primary antibodies were used: anti-beta actina (A-2228, SIGMA), anti-caspase-3 (31A1067, Alexis), anti-caspase-7 (#9492, Cell Signalling) and anti-PARR (#9542S, Cell Signalling).

9.2 FACS Analysis and PI Staining and PI/Annexin V Staining Analyses

For the purpose of determining the effect of the extract of the invention on the cell cycle, a FACS analysis was performed.

For staining with propidium iodide (PI), the cells were seeded in 6-well plates at a density of $10^4$ cells/ml. After 24 h, the tumour cells were treated with indicated concentrations of the extract of the invention for various time intervals. The cells were collected in suspension and the adhered cells were washed in PBS, fixed with frozen ethanol (70% v/v) and stored at −20° C. For the analyses, the cells were washed in PBS 1× and suspended in a solution of PBS 1Z, PI (25 mg/ml) and RNasi A (200 mg/ml).

For the PI/annexin V double staining, the treated cells were collected and resuspended in binding buffer (HEPES pH 7.4, CaCl2 2.5 mM, NaCl 140 mM). Aliquots of cells were incubated per 15 min with annexin V FITC and PI (5 mg/mL) (Invitrogen).

During all the FACS analyses, $10^5$ events were analysed for each sample. The flow cytometry analyses were performed on a GuavaEasyCyte 8HT (Millipore) flow cytometer.

Figure 25:
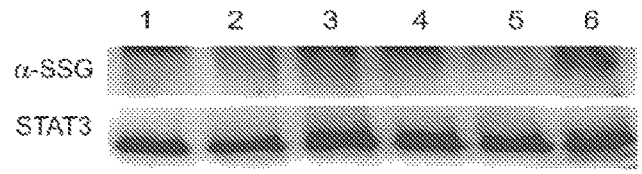

As can be seen in FIG. 25, the extract of the invention induces apoptosis in MSTO211H cells, as determined by the annexin V staining, in a time-dependent and dose-dependent manner.

11. Assay on Glutathione

The variation of the cell redox state, caused by the variation of the ratio between reduced and oxidised glutathione, determines the glutathionylation of STAT3, preventing the phosphorylation thereof in tyrosine and consequently the activation thereof (Butturini E et al. PLoSOne. 2011; 6(5):e20174).

11.1 Intracellular Analyses of GSH.

The intracellular concentration of GSH was evaluated by means of a colorimetric method. The cell extract, deproteinised by means of 10% trichloroacetic acid, was treated with dithio nitrobenzene (DTNB), and the quantity of TNB, which is released following the reaction with GSH, was evaluated by analysing the absorbance at 412 nm.

11.2 Glutathionylation of STAT3

STAT3 was immunoprecipitated by incubating the protein cell extract overnight with an anti-STAT3 antibody. The proteins obtained were separated by means of SDS-PAGE in non-reducing conditions and were transferred on PVDF membrane. The glutathionylated STAT3 was recognised using an anti-GSH antibody.

Figure 24:
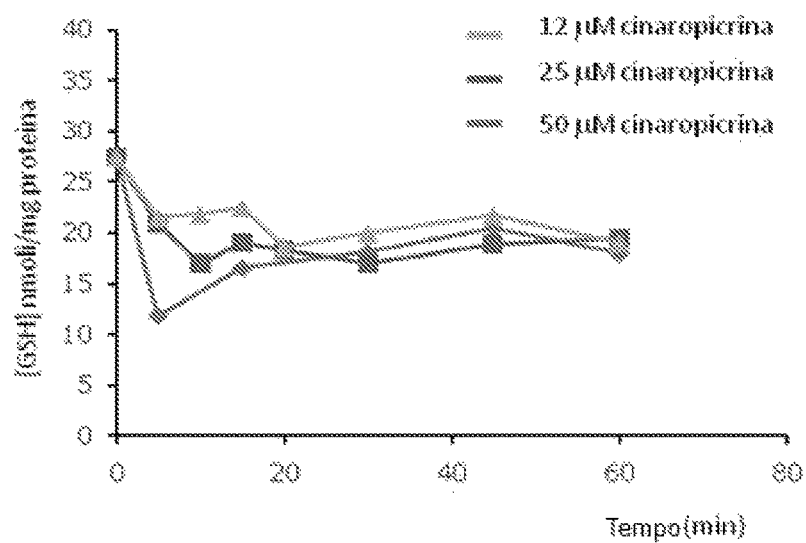

The data shown in FIGS. 24 and 25 demonstrate that cynaropicrin lowers the intracellular concentration of GSH (FIG. 24) and that the variation of the redox state induces the glutathionylation of STAT3, preventing the phosphorylation thereof (FIG. 25). The restoration of the physiological values of GSH, by means of pre-treatment with glutathione ethylene ester, reverses the ability of cynaropicrin to inhibit the phosphorylation of STAT3.

12. Transplantation of Tumour Cells Treated or Untreated with the Extract of the Invention Description of the First Engraftment Experiment.

The MSTO211H cells were treated with artichoke at the concentration of 50 µg/ml for 24 hours. A suspension of $2 \times 10^6$ of cells in PBS/Matrigel (BD Biosciences) was collected and inoculated in the right hip of nude female mice 4 weeks old. The volume of the tumours was monitored twice a week up to the $21^{st}$ day. The mice were sacrificed and the masses removed.

13. Transplantation of Tumour Cells in Mice and Treatment with *Cynara scolymus* and Pemetrexed Description of the Second Engraftment Experiment.

The cells were expanded prior to the implantation and were evaluated in terms of their vitality and contamination, that is to say were counted and resuspended in PBS at a concentration of $20 \times 10^6$/ml. Matrigel was added to the suspension to obtain a final concentration of $10 \times 10^6$ cells/ml of PBS Matrigel 1/1. The MSTO cells were inoculated under the skin in 48 mice.

When the tumour reached an average volume of 60 mm$^3$, the mice were divided into 8 groups formed by 6 animals per group receiving different treatments.

Two groups received artichoke in drinking water for 7 days of the week during a period of three weeks; the other groups received pemetrexed intraperitoneally for 5 days of the week during a period of 3 weeks.

The groups have been outlined in this way in Table 5 below:

|  | no. animals | cell line | no. cells | pathway | volume | treatm. A | start of treatm. |
|---|---|---|---|---|---|---|---|
| Group 1 | 6 | MSTO | $2 \times 10^6$ | SC | 0.2 (matrigel) | | |
| Group 2 | 6 | MSTO | $2 \times 10^6$ | SC | 0.2 (matrigel) | | |
| Group 3 | 6 | MSTO | $2 \times 10^6$ | SC | 0.2 (matrigel) | | |
| Group 4 | 6 | MSTO | $2 \times 10^6$ | SC | 0.2 (matrigel) | | |
| Group 5 | 6 | MSTO | $2 \times 10^6$ | SC | 0.2 (matrigel) | Pemetrexed (100 mg/kg) | after tumour appearance |
| Group 6 | 6 | MSTO | $2 \times 10^6$ | SC | 0.2 (matrigel) | Pemetrexed (100 mg/kg) | after tumour appearance |
| Group 7 | 6 | MSTO | $2 \times 10^6$ | SC | 0.2 (matrigel) | Pemetrexed (100 mg/kg) | after tumour appearance |
| Group 8 | 6 | MSTO | $2 \times 10^6$ | SC | 0.2 (matrigel) | Pemetrexed (100 mg/kg) | after tumour appearance |

|  | administrat. method | treatm. regime | treatm. B | start of treatm. | administrat. method | treatm. regime |
|---|---|---|---|---|---|---|
| Group 1 | | | Cynara extract 20 µg/ml | after tumour appearance | OS | drinking water |
| Group 2 | | | Cynara extract 50 µg/ml | after tumour appearance | OS | drinking water |
| Group 3 | | | Cynara extract 750 µg/ml | after tumour appearance | OS | drinking water |
| Group 4 | | | | | | |
| Group 5 | IP | 5 days in succession | Cynara extract 20 µg/ml | after tumour appearance | OS | drinking water |
| Group 6 | IP | 5 days in succession | Cynara extract 50 µg/ml | after tumour appearance | OS | drinking water |

-continued

| | | | | | | |
|---|---|---|---|---|---|---|
| Group 7 | IP | 5 days in succession | Cynara extract 750 µg/ml | after tumour appearance | OS | drinking water |
| Group 8 | IP | 5 days in succession | | | | |

SC = subcutaneous
treatm. = treatment
administrat. = administration
IP = intraperitoneal
OS = oral With appearance of progression of the tumour (that is to say when the tumour reached 60 mm$^3$), treatment was started with Abo1 and pemetrexed administered as follows: pemetrexed at a dose of 100 mg/Kg in 88 ml/mouse for 5 consecutive days intraperitoneally), artichoke extract in drinking water at concentrations of 25, 50 and 75 micrograms/ml and measured on alternate days for a period of 3 weeks.

The mice were monitored daily to evaluate any signs; body weight was monitored twice weekly.

At the end of the experiment (42 days after inoculation), the tumour masses were collected and fixed in 10% formalin (transferred after 24 hours to 70% ethanol).

The tumour diameters were measured twice weekly using a Mitutoyo caliper.

BIBLIOGRAPHY

Aggarwal B. B. et al. Ann. N.Y. Acad. Sci. 1091; 151-69: 2006
Johnston P A e Grandis R G, MolInterv; 11 (1); 18-26: 2011
Niu G. et al. Mol Cancer Res, 6 (7); 1099-105: 2008
Turkson J. Jove R. "STAT proteins: novel molecular targets for cancer drug discovery" Oncogene. 2000 Dec. 27; 19(56):6613-26
Yu. H. et al "STATs in cancer inflammation and immunity: a leading role for STAT3" Nature Reviews Cancer 9, 798-809 (November 2009)

What is claimed is:

1. A method for treating a condition selected from the group consisting of prostate cancer, multiple myeloma, leukemia, lymphoma, melanoma, ovarian carcinoma, renal carcinoma, pancreatic adenocarcinoma, lung cancer, brain cancer, erythroleukemia, squamous cell carcinoma of the head and neck, colon cancer, and malignant pleural mesothelioma, consisting essentially of administering to a human in need thereof a therapeutically effective amount of an extract of *Cynara cardunculus* subsp. *Scolymus* and a compound selected from the group consisting of cisplatinum, doxorubicin, pemetrexed, methotrexate, vinorelbine, gemcitabine, and taxol to effectively treat the condition in said human in need thereof, wherein said administration is systemic.

2. The method of claim 1, wherein said extract of *Cynara cardunculus* subsp. *Scolymus* is a dry, a lyophilized or a fluid extract from leaves or flower heads of the *Cynara cardunculus* subsp. *Scolymus*.

3. The method of claim 1, wherein said condition which is selected from the group consisting of prostate cancer, multiple myeloma, leukemia, lymphoma, melanoma, ovarian carcinoma, renal carcinoma, pancreatic adenocarcinoma, lung cancer, brain cancer, erythroleukemia, squamous cell carcinoma of the head and neck, colon cancer, and malignant pleural mesothelioma tumor is resistant to treatment with chemotherapeutic agents that do not inhibit signal transducer and activator of transcription.

* * * * *